US010350572B2

(12) United States Patent
Locke et al.

(10) Patent No.: US 10,350,572 B2
(45) Date of Patent: Jul. 16, 2019

(54) SIMULTANEOUS ON-SITE PRODUCTION OF HYDROGEN PEROXIDE AND NITROGEN OXIDES FROM AIR AND WATER IN A LOW POWER FLOWING LIQUID FILM PLASMA DISCHARGE FOR USE IN AGRICULTURE

(71) Applicant: Florida State University Research Foundation, Inc., Tallahassee, FL (US)

(72) Inventors: Bruce R. Locke, Tallahassee, FL (US); Robert Wandell, Tallahassee, FL (US)

(73) Assignee: FLORIDA STATE UNIVERSITY RESEARCH FOUNDATION, INC., Tallahassee, FL (US)

( * ) Notice: Subject to any disclaimer, the term of this patent is extended or adjusted under 35 U.S.C. 154(b) by 223 days.

(21) Appl. No.: 15/125,321

(22) PCT Filed: Mar. 13, 2015

(86) PCT No.: PCT/US2015/020475
§ 371 (c)(1),
(2) Date: Sep. 12, 2016

(87) PCT Pub. No.: WO2015/138921
PCT Pub. Date: Sep. 17, 2015

(65) Prior Publication Data
US 2017/0021326 A1    Jan. 26, 2017

Related U.S. Application Data

(63) Continuation-in-part of application No. 14/213,068, filed on Mar. 14, 2014, now Pat. No. 9,861,950.
(Continued)

(51) Int. Cl.
*B01J 19/08*    (2006.01)
*C05C 5/00*    (2006.01)
(Continued)

(52) U.S. Cl.
CPC ............ *B01J 19/088* (2013.01); *C05C 5/00* (2013.01); *C07C 29/48* (2013.01);
(Continued)

(58) Field of Classification Search
None
See application file for complete search history.

(56) References Cited

U.S. PATENT DOCUMENTS

| 1,708,126 A | 4/1929 | Wilhelm Esmarch |
| 2,045,343 A | 6/1936 | Darrah |

(Continued)

FOREIGN PATENT DOCUMENTS

| CA | 1069857 A | 1/1980 |
| GB | 787748 A | 12/1957 |

(Continued)

OTHER PUBLICATIONS

International Search Report dated Jun. 9, 2015 in International Application No. PCT/US2015/020475.
(Continued)

*Primary Examiner* — Kishor Mayekar
(74) *Attorney, Agent, or Firm* — Fox Rothschild LLP

(57) ABSTRACT

A reactor system that includes a single reactor or a plurality of parallel reactors. A method that includes injecting a mixture including liquid water and a gas, into at least one electrically-conductive inlet capillary tube of a continuously-flowing plasma reactor to generate a flowing liquid film region on one or more internal walls of the continuously-flowing plasma reactor with a gas stream flowing through the flowing liquid film region; propagating a plasma discharge along the flowing liquid film region from at least one electrically-conductive inlet capillary to an electrically-conductive outlet capillary tube at an opposing end of the continuously-flowing plasma reactor; dissociating the liquid
(Continued)

water in the plasma discharge to form a plurality of dissociation products; producing hydrogen peroxide and nitrogen oxides from the plurality of dissociation products.

9 Claims, 21 Drawing Sheets

Related U.S. Application Data

(60) Provisional application No. 61/953,382, filed on Mar. 14, 2014, provisional application No. 61/784,149, filed on Mar. 14, 2013.

(51) Int. Cl.
    *A01N 59/00*     (2006.01)
    *C07C 29/48*     (2006.01)

(52) U.S. Cl.
    CPC ............... *B01J 2219/0805* (2013.01); *B01J 2219/0845* (2013.01); *B01J 2219/0869* (2013.01); *B01J 2219/0884* (2013.01); *B01J 2219/0894* (2013.01)

(56) References Cited

U.S. PATENT DOCUMENTS

| | | | |
|---|---|---|---|
| 3,205,162 | A | 9/1965 | Maclean |
| 3,497,436 | A | 2/1970 | Yates et al. |
| 4,141,715 | A | 2/1979 | Wyse et al. |
| 4,297,123 | A | 10/1981 | Wyse et al. |
| 4,456,512 | A | 6/1984 | Bieler et al. |
| 4,926,001 | A | 5/1990 | Alagy et al. |
| 6,228,266 | B1 | 5/2001 | Shim |
| 6,909,505 | B2 | 6/2005 | Lucas et al. |
| 6,923,890 | B2 | 8/2005 | Ricatto et al. |
| 7,378,062 | B2* | 5/2008 | Itatani ............... H05H 1/46 422/186.04 |
| 7,604,719 | B2 | 10/2009 | Vanden Bussche et al. |
| 7,919,053 | B2 | 4/2011 | Burlica et al. |
| 8,444,924 | B2 | 5/2013 | Burlica et al. |
| 2004/0116752 | A1 | 6/2004 | Giapis et al. |
| 2006/0060464 | A1 | 3/2006 | Chang |
| 2007/0167638 | A1 | 7/2007 | Brophy et al. |
| 2008/0286169 | A1* | 11/2008 | Meillot ............... F23G 5/02 422/186.03 |
| 2009/0004074 | A1 | 1/2009 | Tonkovich et al. |
| 2009/0297406 | A1 | 12/2009 | Okino et al. |
| 2010/0220182 | A1* | 9/2010 | Krull ............... F23N 5/082 348/83 |
| 2011/0026657 | A1 | 2/2011 | Laberge et al. |
| 2012/0000787 | A1* | 1/2012 | Santilli ............... B01J 19/088 205/334 |

FOREIGN PATENT DOCUMENTS

| | | |
|---|---|---|
| GB | 896113 A | 5/1962 |
| GB | 966406 A | 8/1964 |
| WO | 2012126095 A1 | 9/2012 |
| WO | 2013052548 A2 | 4/2013 |
| WO | 2016096751 A1 | 6/2016 |

OTHER PUBLICATIONS

Niozaki et al., "Micro-plasma technology—direct methane to-methanol in extremely confined environment", Natural Gas Conversion VII (2004) 147: 505-510.

Agiral et al., "Gas-to-liquids process using multi-phase flow, non-thermal plasma microreactor", Chemical Engineering Journal (2011) 167: 560-566.

Akiyama, "Streamer discharges in liquids and their applications", IEEE Transactions on Dielectrics and Electrical Insulation (2000) 7: 646-653.

Bie et al., "Dielectric barriers discharges used for the conversion of greenhouse gases: Modeling the plasma chemistry by fluid simulations", Plasma Sources Science & Technology (2011) 20(2): 024008. (12 pages).

Bie et al., "Fluid modeling of the conversion of methane into higher hydrocarbons in an atmospheric pressure dielectric barrier discharge", Plasma Processes and Polymers (2011) 8: 1033-1058.

Bruggeman et al., "Non-thermal plasmas in and in contact with liquids", Journal of Physics D: Applied Physics (2009) 42: 1-28.

Burlica et al., "Formation of H2 and H2O2 in water-spray gliding arc nonthermal plasma reactor", Industrial & Engineering Chemistry Research (2010) 49(14): 6342-6349.

Burlica et al., "Hydrogen generation by pulsed gliding arc discharge plasma with sprays of alcohol solutions", Industrial & Engineering Chemistry Research (2011) 50: 9466-9470.

Burlica et al., "Pulsed plasma gliding arc discharges with water spray", IEEE Transactions on Industry Applications (2008) 44: 482-489.

Davies et al., "Glow-discharge electrolysis. Part I. The Anodic formation of hydrogen peroxide in inert electrolytes", Journal of the Chemical Society, Faraday Transactions (Sep. 1952): 3595-3602.

Friedrich, "Mechanisms of plasma polymerization—Reviewed from a chemical point of view", Plasma Processes and Polymers (2011) 8: 783-802.

Gambus et al., "Oxidation of long chain hydrocarbons by means of low-pressure plasmas", Energy & Fuels (2001) 15: 881-886.

Gesser et al., "The direct conversion of methane to methanol by controlled oxidation", Chemical Reviews (1985) 85: 235-244.

Goujard et al., "Plasma-assisted partial oxidation of methane at low temperatures: Numerical analysis of gas-phase chemical mechanism", Journal of Physics D-Applied Physics (2011) 44(27): 274011. (13 pages).

Hickling et al., "Contact glow-discharge electrolysis", Transactions of the Faraday Society (1964) 60: 783-793.

Hickling, "Electrochemical processes in glow discharge at the gas-solution interface", Modem Aspects of Electrochemistry (1971) 6: 329-373.

Hijikata et al., "Methanol conversion from methane and water vapor by electric discharge (effect of electric discharge process on methane conversion)", Heat Transfer Asian Research (1999) 28: 404-417.

Honorato et al., "(1)H low- and high-field NMR study of the effects of plasma treatment on the oil and water fractions in crude heavy oil", Fuel (2012) 92: 62-68.

Hsieh et al., "Optical diagnostics of electrical discharge water-spray reactors for chemical synthesis", IEEE Transactions on Industry Applications (2013) 49: 305-310.

Hueso et al., "Water plasmas for the revalorisation of heavy oils and cokes from petroleum refining", Environmental Science & Technology (2009) 43: 2557-2562.

Indarto, "A review of direct methane conversion to methanol by dielectric barrier discharge", IEEE Transactions on Dielectrics and Electrical Insulation (2008) 15: 1038-1043.

Jannini et al., "Hydrogen peroxide oxidation of alkanes catalyzed by the vanadate ion-pyrazine-2-carboxilic acid system", Petroleum Chemistry (2005) 45: 413-418.

Jia et al., "Catalytic functionalization of arenes and alkanes via C-H bond activation", Accounts of Chemical Research (2001) 34: 633-639.

Kamata et al., "Efficient stereo- and regioselective hydroxylation of alkanes catalysed by a bulky poloxometalate", Nature Chemistry (2010) 2: 478-483.

Khani et al., "Investigation of cracking by cylindrical dielectric barrier discharge reactor on the n-hexadecane as a model compound", IEEE Transactions on Plasma Science (2011) 39: 1807-1813.

Kobayashi et al., "The effect of spraying of water droplets and location of water droplets on the water treatment by pulsed discharge in air", IEEE Transactions on Plasma Science (2010) 38: 2675-2680.

(56) References Cited

OTHER PUBLICATIONS

Kozlov et al., "The kinetics and mechanisms of cyclohexane oxygenation by hydrogen peroxide catalyzed by a binuclear iron complex", Russian Journal of Physical Chemistry (2003) 77: 575-579.
Kudryashov et al., "Oxidation of hydrocarbons in a barrier discharge reactor", High Energy Chemistry (2000) 34: 112-115.
Kudryashov et al., "Oxidation of hydrocarbons in a bubble plasma reactor", Petroleum Chemistry (2004) 44: 438-440.
Kudryashov et al., "Oxidation of propylene and isobutylene in a reactor with barrier discharge", Russian Journal of Applied Chemistry (2004) 77: 1904-1906.
Kudryashov et al., "Oxidation of propylene with air in barrier discharge in the presence of octane", Russian Journal of Applied Chemistry (2011) 84: 1404-1407.
Kudryashov et al., "Oxidative conversion of cyclohexane in discharge plasma maintained with different high-voltage power sources", High Energy Chemistry (2008) 42: 51-55.
Kudryashov et al., "Simulation of the kinetics of cyclohexane oxidation in a barrier discharge reactor", High Energy Chemistry (2002) 36: 349-353.
Kudryashov et al., "Study of the products of Benzene Transformation in the presence of argon, hydrogen, and propane-butane mixture in barrier discharge", Petroleum Chemistry (2012) 52: 60-64.
Kudryashov et al., "Transformations of n-hexane and cyclohexane by barrier discharge processing in inert gases", High Energy Chemistry (2001) 35: 120-122.
Labinger et al., "Understanding and exploiting C-H bond activation", Nature (2002) 417: 507-514.
Lee et al., "The characteristics of direct hydroxylation of benzene to phenol with molecular oxygen enhanced by pulse DC corona at atmospheric pressure", Plasma Chemistry and Plasma Processing (2003) 23: 519-539.
Locke et al., "Electrohydraulic discharge and nonthermal plasma for water treatment", Industrial & Engineering Chemistry Research (2006) 45:882-905.
Locke et al., "Elementary chemical and physical phenomena in electrical discharge plasma in gas-liquid environments and in liquids", Plasma Chemistry and Catalysis in Gases and Liquids (2012).
Locke et al., "Review of the methods to form hydrogen peroxide in electrical discharge plasma with liquid water", Plasma Sources Science and Technology (2011) 20: 034006.
Lukes et al., "Aqueous-phase chemistry of electrical discharge plasma in water and in gas-liquid environments", Plasma Chemistry and Catalysis in Gases and Liquids (2012) 1st ed. (ch. 7): 243-308.
Lukes et al., "Biological effects of electrical discharge plasma in water and in gas-liquid environments", Plasma Chemistry and Catalysis in Gases and Liquids (2012) 1st ed. (ch. 8): 309-352.
Malik et al., "Preliminary studies on formation of carbonaceous products by pulsed spark discharges in liquid Hydrocarbons", Journal of Electrostatics (2008) 66: 574-577.
Malik et al., "Water purification by electrical discharges", Plasma Sources Science and Technology (2001) 10: 82-91.
Malik et al., "Water purification by plasmas: Which reactors are most energy efficient", Plasma Chemistry and Plasma Processing (2010) 30: 21-31.
Mandelli et al., "Hydrogen peroxide oxygenation of saturated and unsaturated hydrocarbons catalyzed by montmorillonite or aluminum oxide", Catalysis Letters (2009) 132: 235-243.
Monod et al., "Structure-activity relationship for the estimation of OH-oxidation rate constants of aliphatic organic compounds in the aqueous phase: Alkanes, alcohols, organic acids and bases", Atmospheric Environments (2008) 42: 7611-7622.
Jaramillo-Sierra et al, "Degradation of m-cresol in aqueous solution by dielectric barrier discharge," Journal of Physics; Conference Series 406 (2012) 012025.
Rumbach et al, "Decoupling Interfacial Reactions between Plasmas and Liquids: Charge Transfer vs Plasma Neutral Reactions," J. Am. Chem. Soc. 2013, 135, pp. 16264-16267.
Kuroki et al, "Decomposition of Trace Phenol in Solution Using Gas-Liquid Interface Discharge," Japanese J. of Appl. Phys. vol. 45, No. 5A, 2006, pp. 4296-4300.
Ognier et al, "Analysis of Mechanisms at the Plasma-Liquid Interface in a Gas-Liquid Discharge Reactor Used for Treatment of Polluted Water," Plasma Chem. Plasma Process (2009) 29:261-273.
Magureanu et al, "Degradation of pharmaceutical compound pentoxifylline in water by non-thermal plasma treatment," Water Research 44 (2010) pp. 3445-3453.
Magureanu et al, "Degradation of antibiotics in water by non-thermal plasma treatment," Water Research 45 (2011) pp. 3407-3416.
Lukes et al, "Hydrogen Peroxide and Ozone Formation in Hybrid Gas-Liquid Electrical Discharge Reactors," IEEE Trans. Ind. Appl., vol. 40, No. 1, Jan./Feb. 2004, pp. 60-67.
Locke et al, "Elementary Chemical and Physical Phenomena in Electrical Discharge Plasma in Gas-Liquid Environments and in Liquids," Ch. 6, pp. 185-241 of Plasma Chemistry and Catalysis in Gases and Liquids, 1st ed., Parvulescu et al eds., 2012.
Mora et al., "Selectivity control in a microwave surface-wave plasma reactor for hydrocarbon conversion", Plasma Processes and Polymers (2011) 8: 709-717.
Nozaki et al., "A single step methane conversion into synthetic fuels using microplasma reactor", Chemical Engineering Journal (2011) 166: 288-293.
Nozaki et al., "Innovative methane conversion technology using atmospheric pressure non-thermal plasma", Journal of the Japan Petroleum Institute (2011) 54: 146-158.
Nozaki et al., "Micro-plasma technology—direct methane-to-m ethanol in extremely confined environment", Natural Gas Conversion VII (2004) 147: 505-510.
Nozaki et al., "Partial oxidation of methane using microscale non-equilibrium plasma reactor", Catalysis Today (2004) 98: 607-616.
Nozaki et al., "Selective conversion of methane to synthetic fuels using dielectric barrier discharge contacting liquid film", Journal of Physics D-Applied Physics (2011) 44.
Okazaki et al., "Direct conversion from methane to methanol for high efficiency energy system with exergy regeneration", Energy Conversion and Management (2002) 43: 1459-1468.
Patino et al., "Oxidation of cycloalkanes and diesel fuels by means of oxygen low pressure plasmas", Energy & Fuels (2002) 16: 1470-1475.
Patino et al., "Upgrading of diesel fuels and mixtures of hydrocarbons by means of oxygen low pressure plasmas: A comparative study", Fuel (2003) 82:1613-1619.
Perevezentsev et al., "Transformations of benzene-argon mixture in barrier discharge", High Energy Chemistry (2011)45: 62-65.
Prieto et al., "Nonthermal plasma reactors for the production of light hydrocarbon olefins from heavy oil", Brazilian Journal of Chemical Engineering (2003) 20: 57-61.
Prieto et al., "Reforming of heavy oil using nonthermal plasma", IEEE Transaction on Industry Applications (2001) 37: 1464-1467.
Rasmussen et al., "Direct partial oxidation of natural gas to liquid chemicals: Chemical kinetic modeling and global optimization", Industrial & Engineering Chemistry Research (2008) 47: 6579-6588.
Sedelmeier et al., "KMnO4-mediation oxidation as a continuous flow process", Organic Letters (2010) 12: 3618-3621.
Sekiguchi et al., "Direct hydroxylation of benzene using micro plasma reactor", Kagaku Kogaku Ronbunshu (2004) 30: 183-185. (abstract translation).
Shul'pin et al., "Alkane oxygenation with H2O2 catalysed by FECI3 and 2,2'-bipyridine", Tectrahedron Letters (2005) 46: 4563-4567.
Sivaramakrishnan et al., "Rate constants for OH with selected large alkanes: Shock-tube measurements and an Improved group scheme", Journal of Physical Chemistry A (2009) 113: 5047-5060.
Sprengnether et al., "Rate constants of nine C6-C9 alkanes with OH from 230 to 379 K: Chemical tracers for OH", Journal of Physical Chemistry A (2009) 113: 5030-5038.

(56) References Cited

OTHER PUBLICATIONS

Sugai et al., "Improvement of efficiency for decomposition of organic compounds in water using pulsed streamer discharge in air with water droplets by increasing residence time", Pulsed Power Conference (2009): 1056-1060.
Suhr et al., "Organic syntheses under plasma conditions", Pure and Applied Chemistry (1974) 39: 395-414.
Suss-Fink et al., "Alkane oxidation with hydrogen peroxide catalyzed homogeneously by vanadium-containing polyphosphomolybdates", Applied Catalysis A-General (2001) 217: 111-117.
Suzuki et al., "Investigation of a pulse circuit design and pulse condition for the high energy efficiency on water treatment using pulsed power discharge in a water droplet spray", IEEE Transactions on Dielectrics and Electrical Insulation (2011) 18: 1281-1286.
Takale et al., "Oxidation of dihydrazones of diarylacetylenes using sodium periodate", Chemistry Letters (2010) 39: 1279-1280.
Tezuka et al., "Oxidation of aromatic hydrocarbons with oxygen in a radiofrequency plasma", Plasma Chemistry and Plasma Processing (1996) 16:329-340.
Tezuka et al., "Oxidation of cycloalkanes in a radiofrequency plasma", Bulletin of Chemical Society of Japan (1991) 64: 1063-1065.
Thagard et al., "Electrical discharges in polar organic liquids", Plasma Processes and Polymers (2009) 6: 741-750.
Thornton et al., "Hydrazine synthesis in silent electrical discharge", Advances in Chemistry Series (1969): 165.
Thornton et al., "Hydrazine synthesis in silent electrical discharge", Nature (1967) 213: 1118.
Thornton et al., "Synthesis of formaldehyde from methane in electrical discharges", Nature (Feb. 11, 1967) 213: 590-591.
Sergio et al., "Synthesis of formaldehyde from methane and water in an electrical discharge 2-phase reactor", Journal of Applied Chemistry (1967) 17:325.
Wilson et al., "Measurement and estimation of rate constants for the reactions of hydroxyl radical with several alkanes and cycloalkanes", Journal of Physical Chemistry A (2006) 110: 3593-3604.
Yaji Ma et al., "Oxidation reactions of aromatic ethenes in solution exposed to low-temperature oxygen plasma", Journal of Photopolymer Science and Technology (2007) 20: 235-238.
Yamamoto et al., "Wet type plasma reactor for incinerator", Conference Record of the 1998 IEEE Industry Applications Conference (1998) 1-3: 1861-1864.
Bresch et al.: "Oxidized Derivatives of n-Hexane from a Water/Argon Continuous Flow Electrical Discharge Plasma Reactor", Plasma Chemistry and Plasma Processing, 35(6) (2015) 553-584.
Hsieh et al.: "Analysis of a gas-liquid film plasma reactor for organic compound oxidation", Journal of Hazardous Materials 317 (2016) 188-197.
Hsieh et al.: "Analysis of hydroxyl radical formation in a gas-liquid electrical discharge plasma reactor utilizing liquid and gaseous radical scavengers", Plasma Processes and Polymers, 14(8) e1600171 (2017).
Ammary, "Nutrients requirements in biological industrial wastewater treatment", African Journal of Biotechnology vol. 3 (4), pp. 236-238, Apr. 2004.
Yang et al.: "Occurrences and removal of pharmaceuticals and personal care products (PPCPs) in drinking water and water/sewage treatment plants: A review", Science of the Total Environment 596-597 (2017) 303-320.
Edward Archer et al.: "The fate of pharmaceuticals and personal care products (PPCPs), endocrine disrupting contaminants (EDCs), metabolites and illicit drugs in a WWTW and environmental waters", Chemosphere 174 (2017) 437-446.
Deblonde et al.: "Emerging pollutants in wastewater: A review of the literature" 2011 International Journal of Hygiene and Environmental Health 214 442-8.
Geissen et al.: 2015 Emerging pollutants in the environment: A challenge for water resource management International Soil and Water Conservation Research 3 57-65.
Fujii et al.: 2007 New POPs in the water environment: distribution, bioaccumulation and treatment of perfluorinated compounds—a review paper Journal of Water Supply Research and Technology-Aqua 56 313-26.
Esler, "Concerning Recalcitrant/Refractory Organic Species and Chemical Oxygen Demand (COD) analysis by two different methods: (a) CODCr (the dichromate method) and (b) TiO2/UV photoelectrochemistry (the PeCOD™ method)", Aqua Diagnostic 2008.
Montes-Grajales D et al.: "Occurrence of personal care products as emerging chemicals of concern in water resources: A review" 2017 Science of the Total Environment 595 601-14.
Mompelat S et al. "Occurrence and fate of pharmaceutical products and by-products, from resource to drinking water" 2009 Environment International 35 803-14.
Macedo S et al.: "Methyl-triclosan and triclosan impact embryonic development of Danio rerio and Paracentrotus ividus" 2017 Ecotoxicology 26 482-9.
Khetan S K et al.: "Human pharmaceuticals in the aquatic environment: A challenge to green chemistry Chemical Reviews" 2007 107 2319-64.

\* cited by examiner

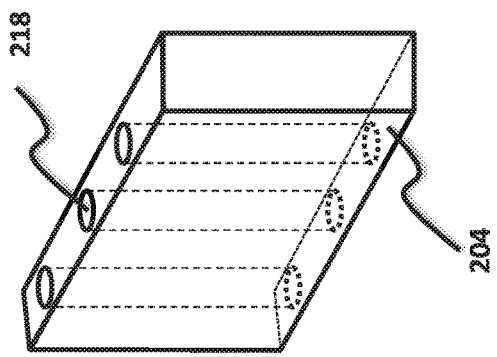
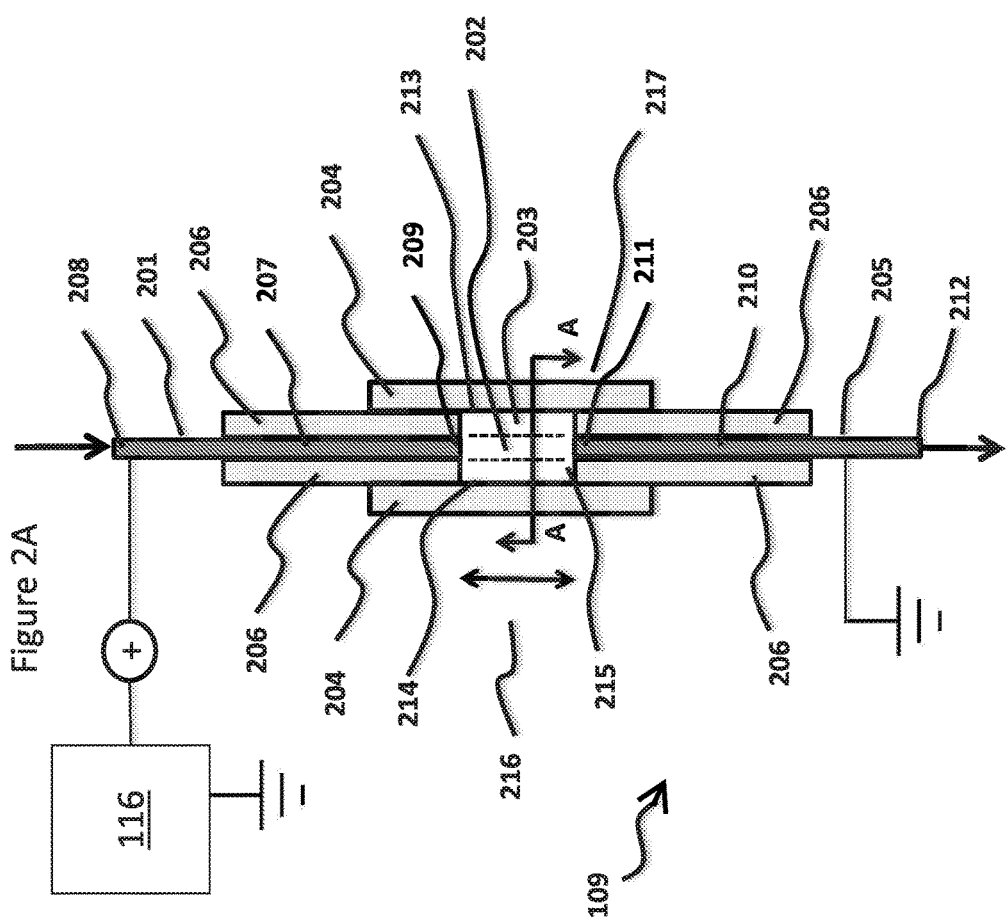

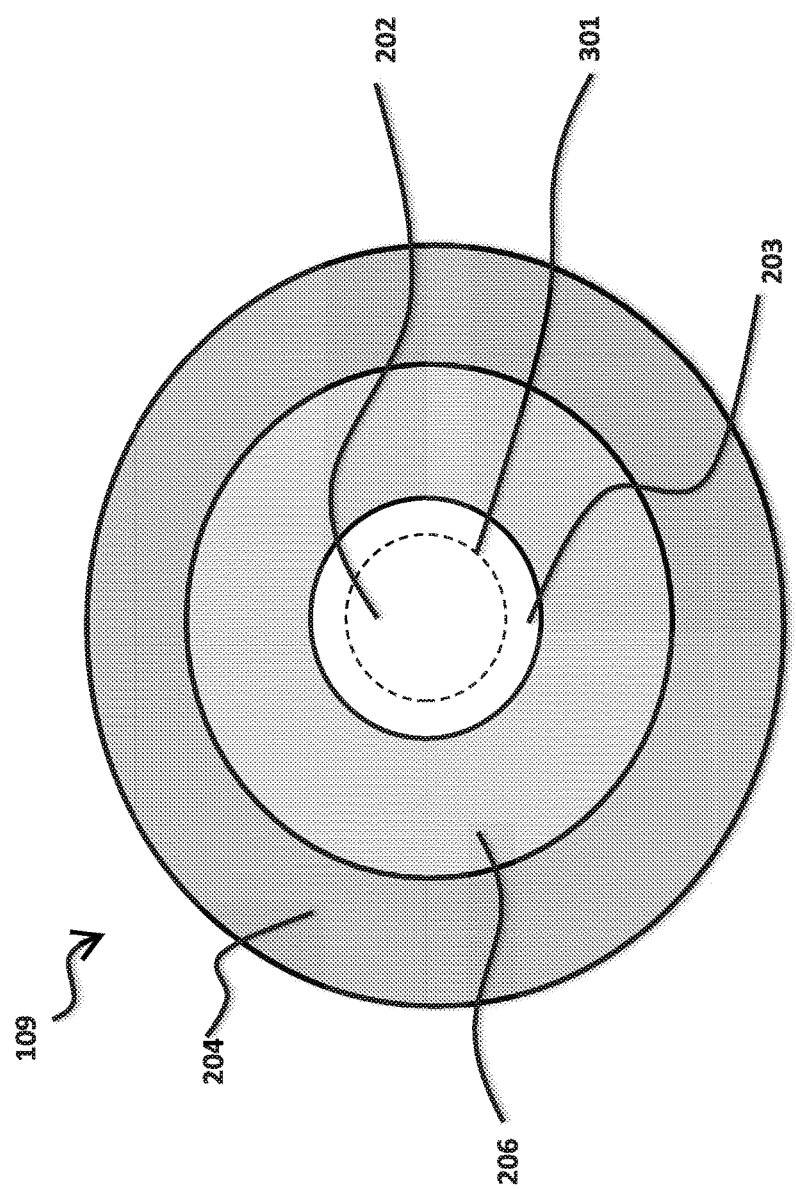

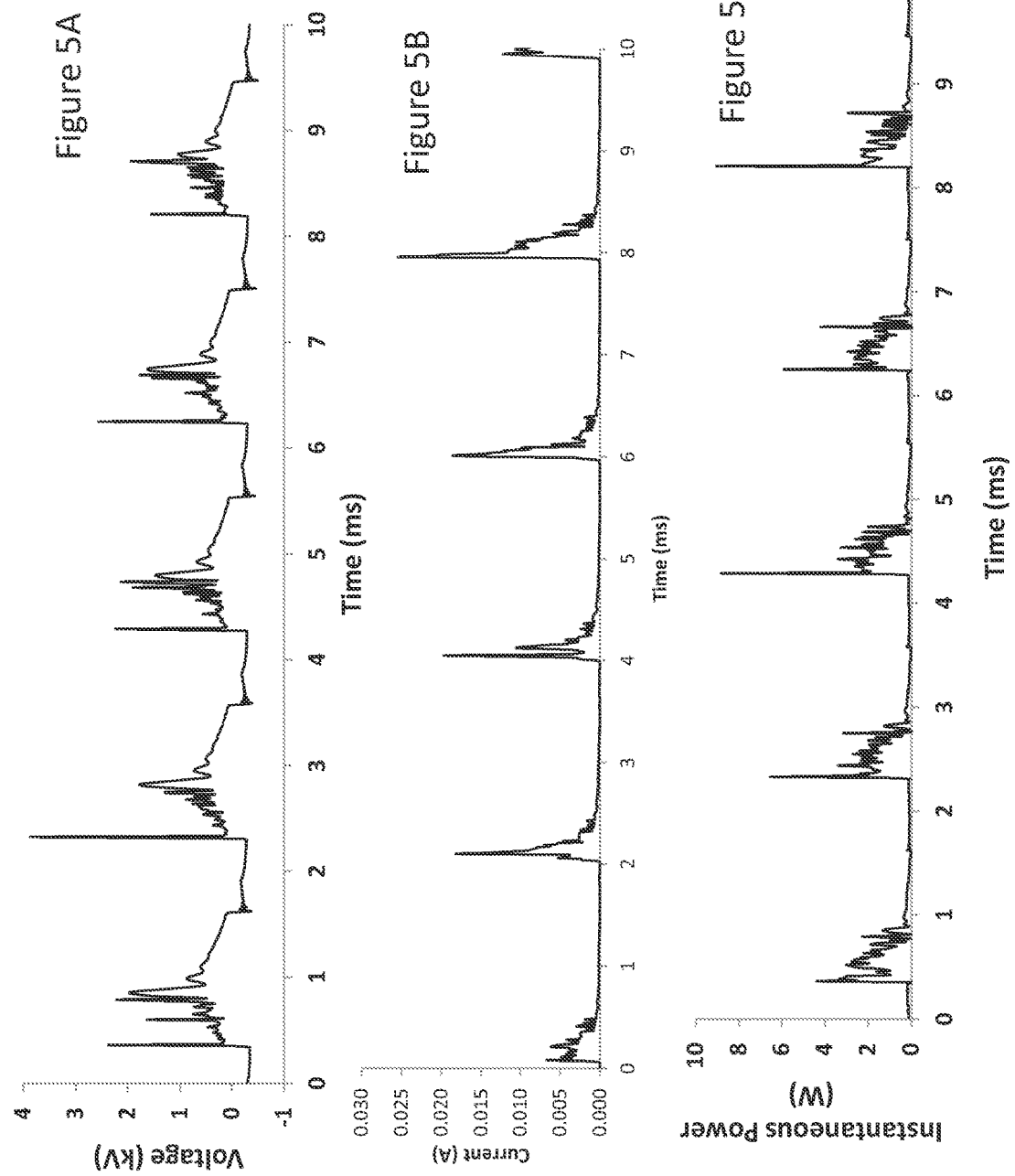

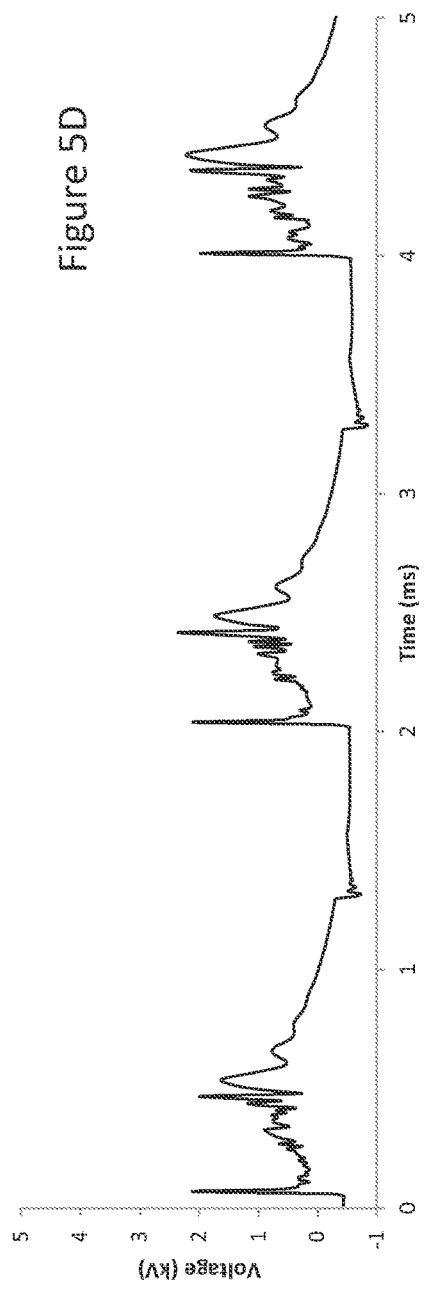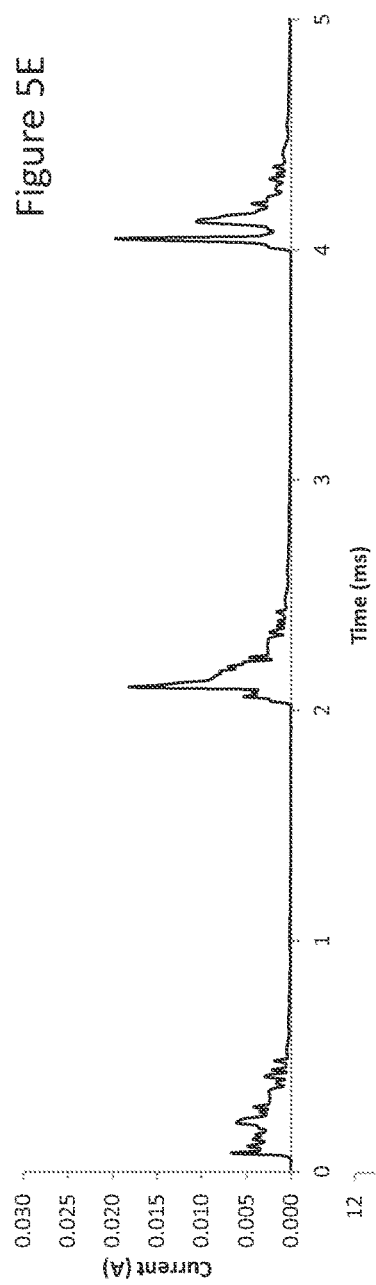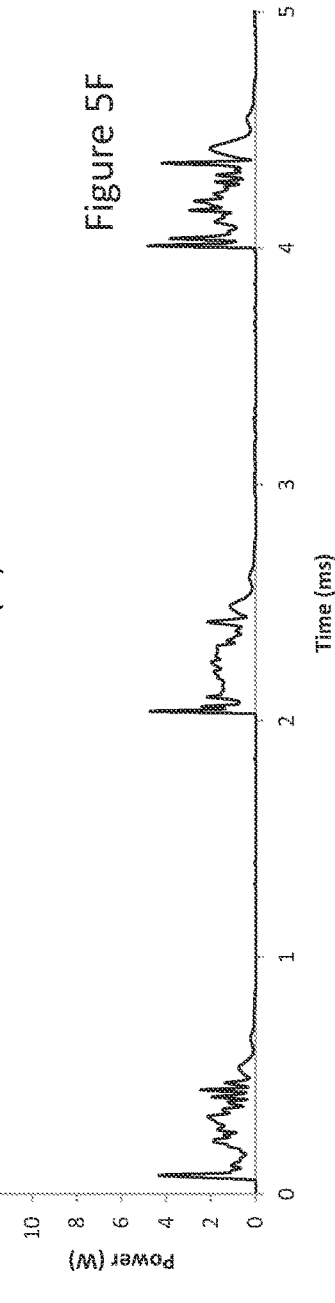

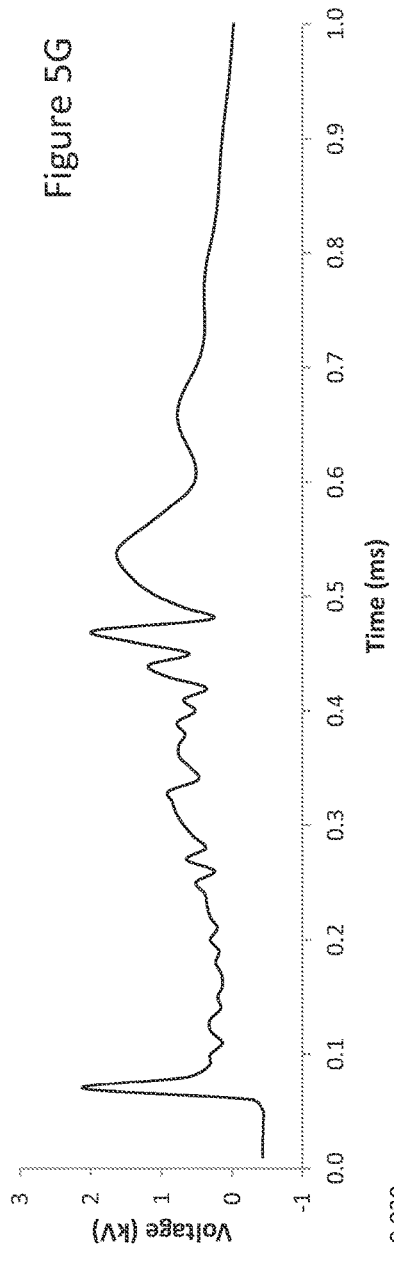
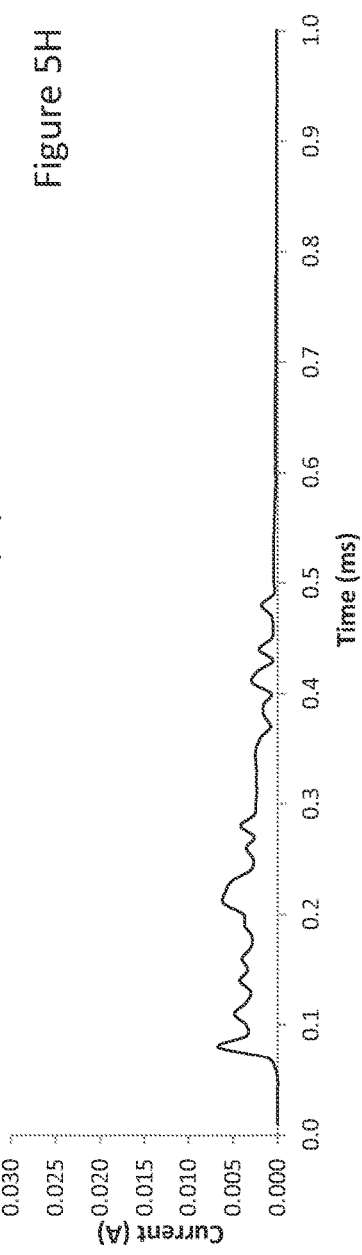
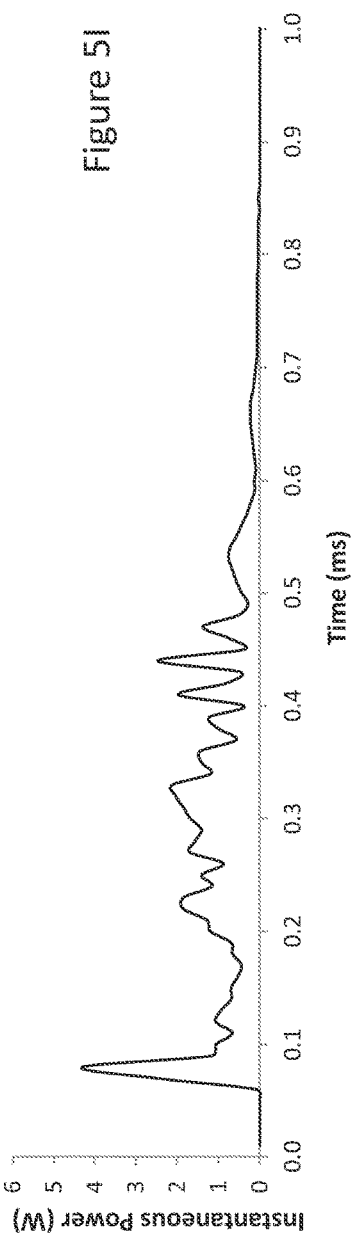

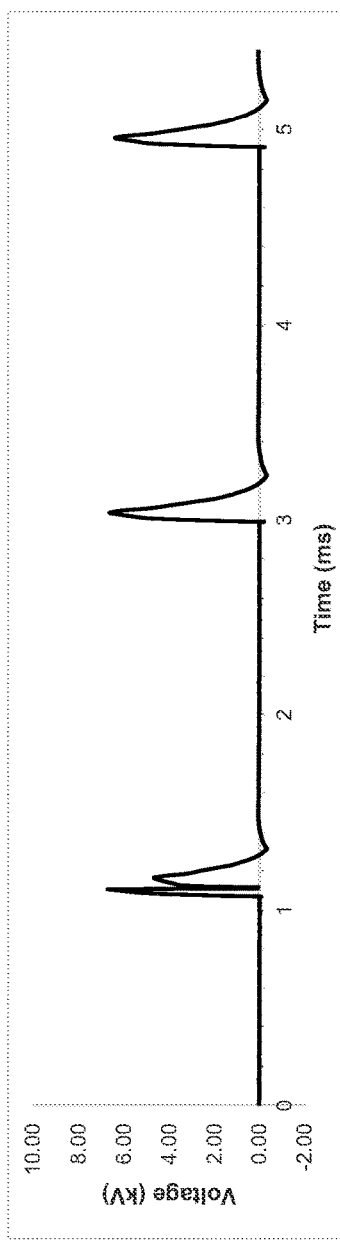
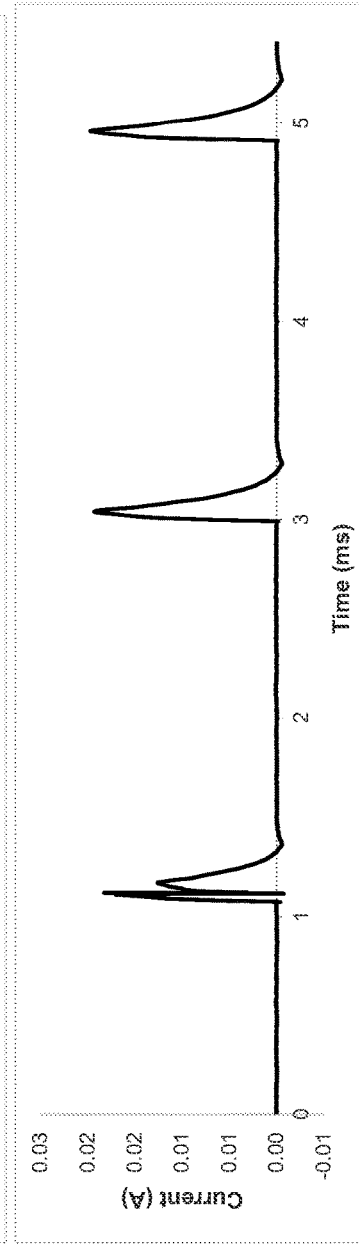
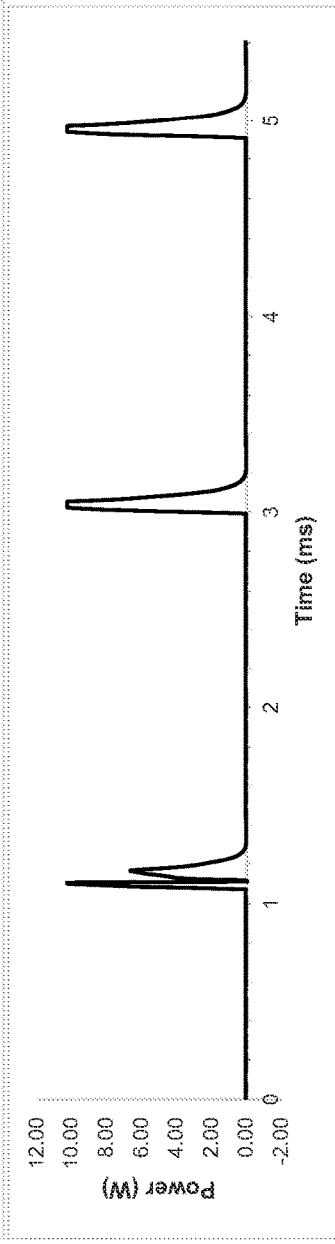

Argon carrier gas (0.3 mL/min)
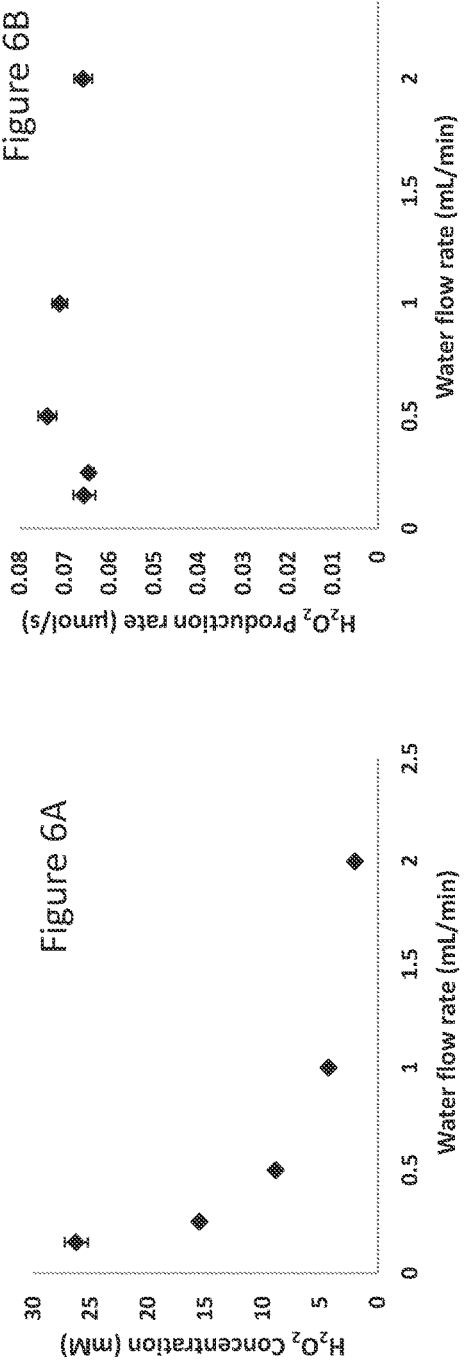
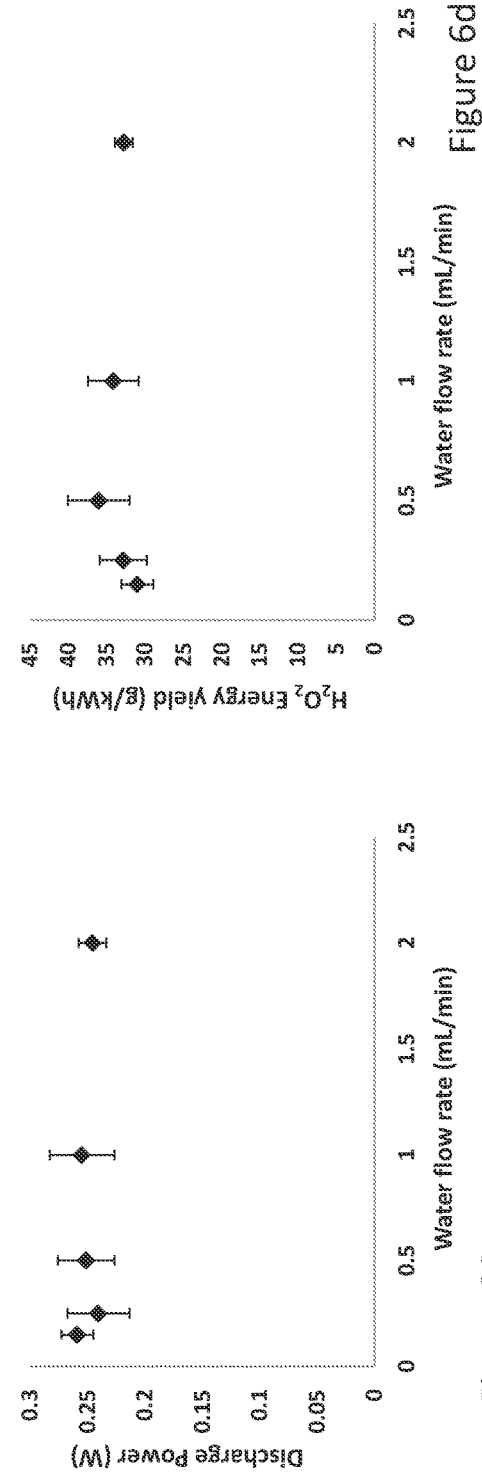
Figure 6A
Figure 6B
Figure 6C
Figure 6d

SIMULTANEOUS ON-SITE PRODUCTION OF HYDROGEN PEROXIDE AND NITROGEN OXIDES FROM AIR AND WATER IN A LOW POWER FLOWING LIQUID FILM PLASMA DISCHARGE FOR USE IN AGRICULTURE

CROSS REFERENCE TO RELATED APPLICATIONS

This application is a National Stage Entry of PCT/US15/20475, filed Mar. 13, 2015, which claims priority to U.S. Provisional Patent Application No. 61/953,382, filed Mar. 14, 2014 entitled SIMULTANEOUS ON-SITE PRODUCTION OF HYDROGEN PEROXIDE AND NITROGEN OXIDES FROM AIR AND WATER IN A LOW POWER FLOWING LIQUID FILM PLASMA DISCHARGE FOR USE IN AGRICULTURE, and to U.S. patent application Ser. No. 14/213,068, filed on Mar. 14, 2014 entitled FORMATION OF ALCOHOLS AND CARBONYL COMPOUNDS FROM HEXANE AND CYCLOHEXANE WITH WATER IN A LIQUID FILM PLASMA REACTOR, which claimed priority to U.S. Provisional Patent Application No. 61/784,149, filed Mar. 14, 2013 entitled ORGANIC CHEMICAL SYNTHESIS USING PLASMA REACTORS WITH LIQUID ORGANIC AND LIQUID WATER, all of which are incorporated herein by reference in their entireties.

STATEMENT REGARDING FEDERALLY SPONSORED RESEARCH OR DEVELOPMENT

This invention was made with government support under Grant No. CBET1236225 awarded by the National Science Foundation. The government has certain rights in the invention.

FIELD OF THE INVENTION

The invention relates generally to the production of hydrogen peroxide and nitrogen oxides, and more specifically to the simultaneous production of hydrogen peroxide and nitrogen oxides from air and water.

BACKGROUND OF THE INVENTION

Nitrate is a form of nitrogen which as a high bioavailability to plant life and is one of the most common components in the fertilizers which are used in agriculture. Because of its high bioavailability, very low concentrations of nitrate fertilizers are commonly dissolved directly into irrigation systems for foliar application to provide a continuous supply of nutrients to the plants and allow more efficient absorption. Hydrogen peroxide can also be used in agriculture for disease prevention and algae control where it too can be added directly into an irrigation system in very low concentrations. It would be desirable to facilitate the simultaneous production of hydrogen peroxide and nitrogen oxides from air and water, particularly for use in agriculture.

BRIEF DESCRIPTION OF THE DRAWINGS

These and other features, aspects, and advantages of the present invention will become better understood with reference to the following description and appended claims, and accompanying drawings where:

FIG. 2A: shows an illustration of a vertical cross section of the plasma reactor according to various embodiments;

FIG. 2B: shows a perspective view illustration of a casing according to various embodiments;

FIG. 3A-D: show illustrations cross sections of various embodiments of the plasma reactor;

FIG. 5A-L: are charts showing sample waveform of discharges;

FIG. 6A-D: are charts showing concentration of hydrogen peroxide (a), production rate of hydrogen peroxide (b), mean discharge power (c), and energy yield (d) for various water flow rates when only argon is used as the carrier gas;

Figure 1A:
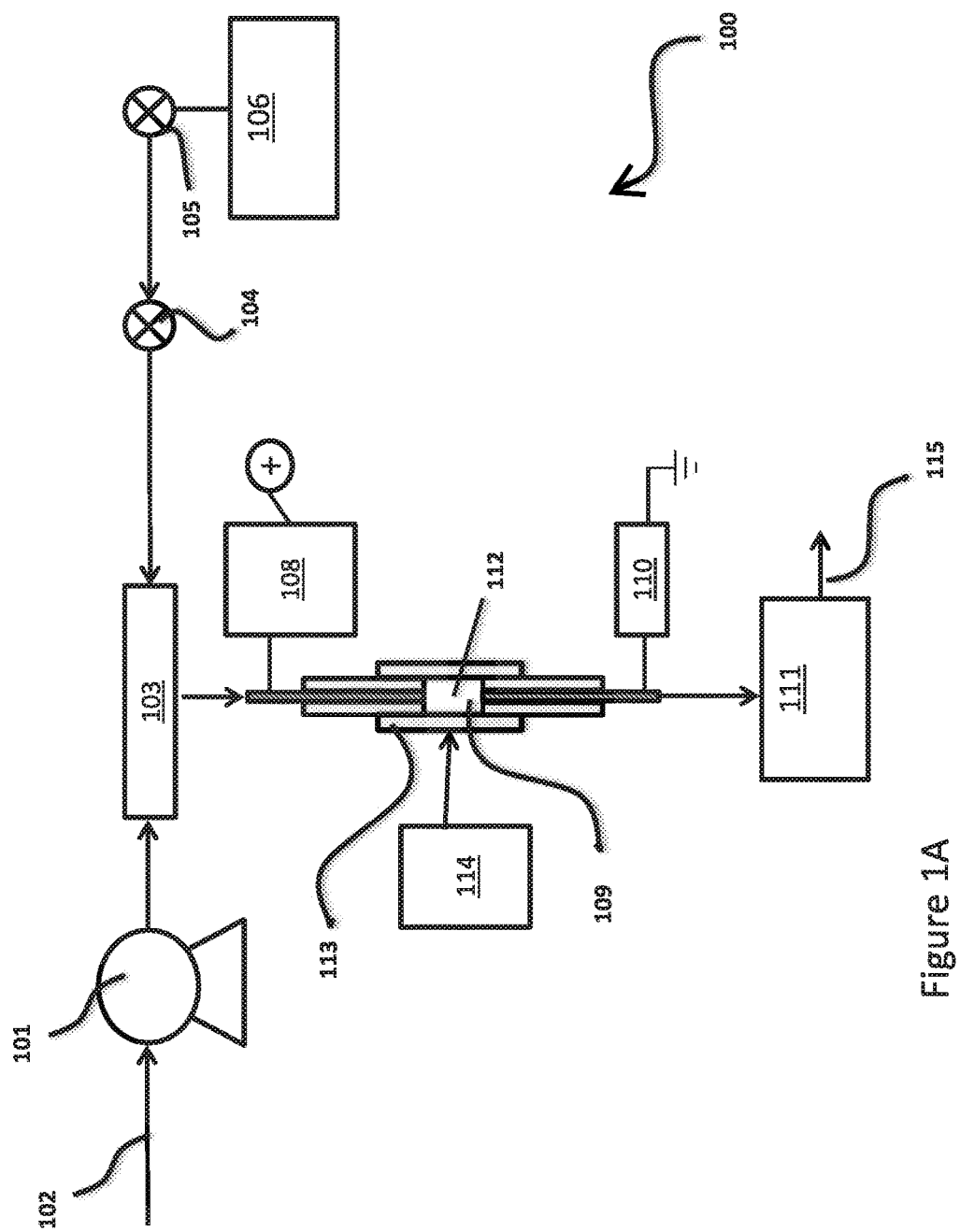
FIG. 1A: is a schematic diagram of a system and process according to various embodiments.

It should be understood that the various embodiments are not limited to the arrangements and instrumentality shown in the drawings.

DETAILED DESCRIPTION OF THE INVENTION

According to various embodiments both air and water are used in a single system to generate both nitrate and hydrogen peroxide simultaneously without the need for other chemical intermediates or stabilizers.

The present invention may be understood more readily by reference to the following detailed description of preferred embodiments of the invention as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Electrical discharge plasma contacting liquid phases has been studied for a wide range of chemical, biomedical, environmental, and materials synthesis applications. The synthesis of a number of organic and inorganic compounds by gas-liquid plasma can involve glow discharge electrolysis whereby one electrode is placed inside the liquid phase and one in the gas phase. A wide range of other gas-liquid contacting schemes has been studied including falling films, aerosol sprays, and bubble injection into liquids. It has been shown that the presence of the liquid phase not only affects plasma properties such as electron energy and density, but also the chemical reactions which take place. The liquid phase can also serve as a source of additional vapor phase reactant as well as function as a reservoir to collect the generated products, protecting those products from degradation by direct electron attack in the gas phase plasma.

For chemical synthesis in gas-liquid plasma discharges the reactions that occur depend on the chemical makeup of both the liquid and the carrier gas. In the simplest case an inert gas can be used in conjunction with water in order to limit the reactive chemical species present to only hydrogen and oxygen. Under these conditions it has been shown that hydrogen peroxide can be generated by the disassociation of the water molecules in the gas phase plasma into hydroxyl radicals. Due to the limited chemistry present in this situation, neighboring hydroxyl radicals combine to form hydrogen peroxide molecules which rapidly dissolve into the liquid phase where they are protected from degradation by the plasma and can be easily collected.

When a non-inert carrier gas is used in conjunction with liquid water the reactive chemical species in the gas stream can react with the hydroxyl radicals formed from the water to generate other oxidized products. When air ($O_2$, $N_2$) is subjected to a plasma discharge $NO_x$ is formed after dissociation of the diatomic species present in the gas. The formed $NO_x$ molecules can then be oxidized into nitrate by hydroxyl radicals. Similar to hydrogen peroxide, the formed nitrate rapidly dissolves into the liquid phase where it is protected from degradation by the plasma and can be easily collected.

Various embodiments relate to a system which can be used on a farm to generate both nitrate and hydrogen peroxide on-site to be introduced directly into an irrigation system where the only chemical feeds required are air and water. Further, by manipulating the flow rates of these reactants into the system the relative concentrations of the generated products can be varied to fit the requirements of specific applications. For applications which require higher hydrogen peroxide concentrations argon gas could be supplemented into the gas phase in order to increase generation.

Various embodiments relate to a method that includes injecting a mixture comprising liquid water and a gas, into at least one electrically-conductive inlet capillary tube of a continuously-flowing plasma reactor to generate a flowing liquid film region on one or more internal walls of the continuously-flowing plasma reactor with a gas stream flowing through the flowing liquid film region; propagating a plasma discharge along the flowing liquid film region from at least one electrically-conductive inlet capillary to an electrically-conductive outlet capillary tube at an opposing end of the continuously-flowing plasma reactor; dissociating the liquid water in the plasma discharge to form a plurality of dissociation products; producing hydrogen peroxide and nitrogen oxides (NO, NO2, NO3) from the plurality of dissociation products; dissolving the hydrogen peroxide and the nitrogen oxides into the flowing liquid film region; and recovering at least a portion of the hydrogen peroxide and the nitrogen oxides from the electrically conductive outlet capillary. The nitrogen oxides and the hydrogen peroxide dissolved into the flowing liquid film region may be protected from degradation as the hydrogen peroxide and the nitrogen oxides flow through the flowing liquid film region and exit the continuously-flowing plasma reactor via the electrically conductive outlet capillary. The mixture may be injected into a plurality of electrically-conductive inlet capillary tubes. The flowing liquid film region may have an annular shape. The plasma discharge may have a nominal frequency of 500 Hz. The plasma discharge may have a frequency of from about 100 to 10,000 Hz. The liquid water may have a temperature of from greater than 0 to less than 100 degrees Celsius and the reactor may have a pressure of from approximately 0.1 to 2 bar. The liquid water may have a conductivity of near 1 microSiemens/cm to 500 microSiemens/cm. The gas may be air. The at least one electrically-conductive inlet capillary and the at least one electrically-conductive outlet capillary may include an electrically conductive material. The electrically conductive material may include stainless steel, nickel alloys, chromium alloys, titanium alloys, molybdenum alloys, copper alloys, gold alloys, platinum alloys, zinc alloys, zirconium alloys, and combinations thereof.

Some embodiments relate to a reactor system that includes a single reactor. Other embodiments relate to a reactor system that may include a casing having a plurality of internal cavities; and a plurality of reactor assemblies arranged in parallel, wherein each of the plurality of reactor assemblies includes: at least one electrically-conductive inlet capillary having an inlet capillary body extending between a fluid-receiving tip and a fluid-injecting tip, wherein the fluid-receiving tip is positioned outside one of the plurality of internal cavities, and wherein the fluid-injecting tip is positioned inside one of the plurality of internal cavities; at least one electrically-conductive outlet capillary having an outlet capillary body extending between a fluid-collecting tip and a fluid-ejecting tip, wherein the fluid-collecting tip is positioned inside one of the plurality of internal cavities, and wherein the fluid-ejecting tip is positioned outside one of the plurality of internal cavities, wherein the fluid injecting tip is disposed relative to the fluid collecting tip to generate a flowing liquid film region on an internal wall of one of the plurality of internal cavities and a gas stream flowing through the flowing liquid film region, when a fluid is injected into the internal cavity via the at least one electrically conductive inlet capillary, and wherein the fluid injecting tip is disposed relative to the fluid collecting tip to propagate a plasma discharge along the flowing liquid film region between the at least one electrically-conductive inlet capillary and the at least one electrically-conductive outlet capillary. The fluid injecting tip may be aligned with the fluid collecting tip. A gap may separate the fluid-injecting tip and the fluid-collecting tip. The gap may have a length, and a ratio of the voltage to the length may be at least about $2.5 \times 10^5$ V/m. The reactor system may also include a power source, supplying a voltage across the at least one electrically-conductive inlet capillary and the at least one electrically-conductive outlet capillary. The power source may be adapted to provide a pulsed current between the at least one electrically-conductive inlet capillary and the at least one electrically-conductive outlet capillary. The power source may be adapted to provide a D.C. current between the at least one electrically-conductive inlet capillary and the at least one electrically-conductive outlet capillary. The power source may be adapted to provide an A.C. current between the at least one electrically-conductive inlet capillary and the at least one electrically-conductive outlet capillary.

FIG. 1A shows a schematic diagram of a system and process 100 according to various embodiments. A high pressure carrier gas may be added to the mixing zone 103 from a high pressure storage container 106 via a pressure regulator 105. The flow rate of the high pressure carrier gas may be measured by a rotameter 104. Simultaneously, deionized (DI) water 102 can be pumped via a pump 101, such as a high-pressure pulse injection pump, into the mixing zone 103. The mixing zone 103 may be any suitable structure. For example, the mixing zone 103 may simply be a tee joint, such as a nylon Swagelok tee joint. After mixing in the mixing zone 103, all of the contents of the mixing zone may be passed to, added to, or injected to a reactor 109. The reactor 109 is illustrated in greater detail in FIG. 2A. Generally speaking, however, when added to the reactor 109, the contents of the mixing zone 103 can generate a flowing liquid film region on one or more internal walls of the reactor 109 with a gas stream flowing through the flowing liquid film region. A power source may supply a voltage across at least one electrically-conductive inlet capillary and at least one electrically-conductive outlet capillary of the reactor. A high voltage (HV) probe 108 can be used to measure the voltage applied to the reactor. At the outlet of the reactor a shunt 110 can be used to measure the electrical current and thereby in combination with the voltage determine the power delivered to the reactor. A plasma discharge may be propagated along the flowing liquid film region from at least one electrically-conductive inlet capillary to an electrically-conductive outlet capillary tube at an opposing end of the continuously-flowing plasma reactor 109. The reactor 109 may, therefore, include a plasma discharge region 112. According to certain preferred embodiments, the plasma discharge region 112 may be bounded by a casing 113. The casing may be optically transparent to allow emission spectroscopy and/or high speed imaging to be performed on the plasma discharge region 112 of the reactor 109 via an imaging apparatus 114. For example, a chemical analysis of the contents of the reactor 109 can be performed using atomic emission spectroscopy (AES), which measures the intensity of light emitted from a flame, plasma, arc, or spark at a particular wavelength to determine the quantity of an element in a sample. As a result of the plasma discharge, the liquid water in the plasma discharge may be dissociated to form a plurality of dissociation products. Hydrogen peroxide and nitrogen oxides (NO, $NO_2$, $NO_3$) may be produced from the plurality of dissociation products. The hydrogen peroxide and the nitrogen oxides may be dissolved into the flowing liquid film region. At least a portion of the hydrogen peroxide and the nitrogen oxides may be recovered from the electrically conductive outlet capillary. For example, a liquid effluent trap 111 may be used to collect the liquid exiting the reactor for use and/or subsequent chemical analysis via a gas effluent exit 115.

Figure 1B:
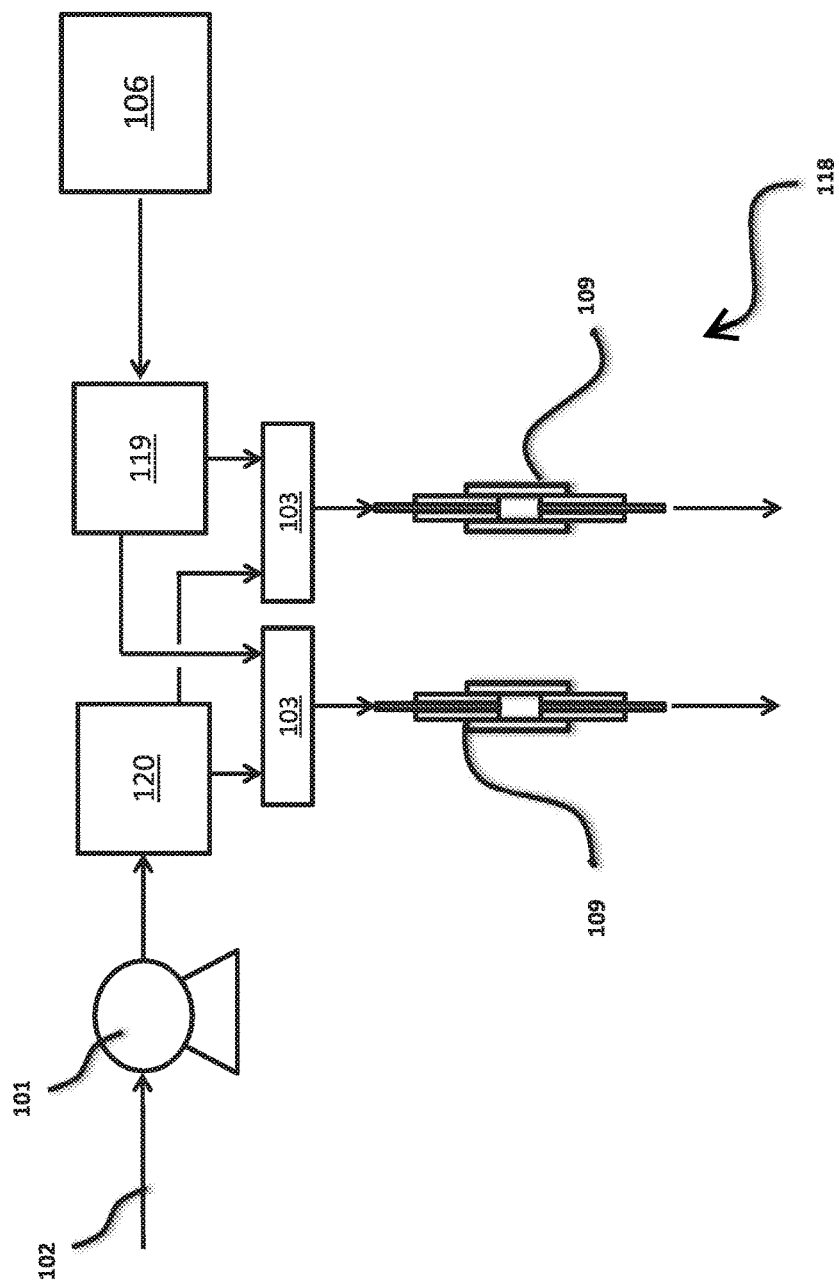
FIG. 1B: is a schematic diagram of a system and process for operating a plurality of reactors in parallel, according to various embodiments.

FIG. 1B illustrates an embodiment of the system and process 118 wherein a plurality of reactors 109 are connected in parallel. All details of the system and process can be the same as those illustrated in FIG. 1A, except as otherwise noted. Any number of reactors 109 may be operated in parallel, although only two reactors 109 are so illustrated. In parallel operation, the high pressure storage container 106 may supply the high pressure carrier gas to a gas splitting region 119, which may divert the high pressure carrier gas stream to a plurality of mixing zones 103. Similarly, the pump 101 may supply the deionized water 102 to a water splitting region 120, which may divert the deionized water 102 to the plurality of mixing zones 103. Just as in the embodiment illustrated in FIG. 1A, the after mixing in each of the plurality of mixing zones 103, the contents of each mixing zone may be passed to, added to, or injected to one of the plurality of reactors 109. The liquid, comprising the reaction products, as described with respect to FIG. 1A, may be discharged from each of the plurality of reactors 109 at an approximately equal flow rate.

Figure 1C:
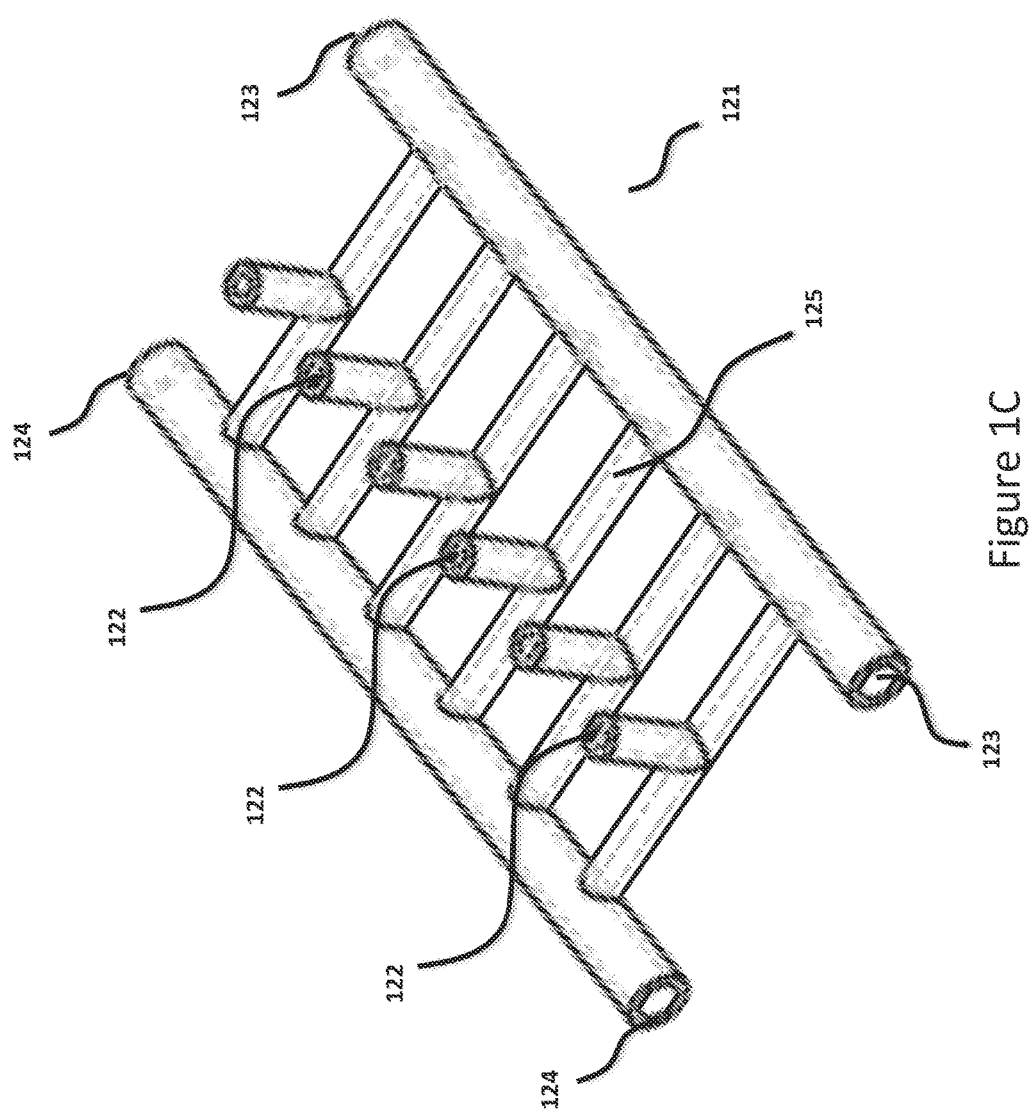
FIG. 1C: is a schematic diagram of a manifold useful for operating a plurality of reactors in parallel, according to various embodiments.

FIG. 1C illustrates a manifold 121 useful in various embodiments wherein a plurality of reactors 109 are connected in parallel. The manifold 121 includes one or more gas inlets 124 and one or more water inlets 123. The one or more gas inlets 124 and the one or more can supply gas and water, respectively, to a plurality of mixing zones 125. Each of the mixing zones 125 may include an outlet 122 for discharging a water/gas mixture to a respective one of the plurality of reactors 109. The manifold 121 may be made from any suitable material. A preferable material is plastic. The manifold 121 may be manufactured by any suitable means, including but not limited to welding, gluing, or 3D printing. As illustrated in FIG. 1C, the manifold 121 can include a plurality of tubular components. The tubular components may be of any suitable size. According to certain embodiments, however, the tubular components may have a wall thickness of about 1/16 inch and an internal diameter of about 1/8 inch.

FIG. 2A shows an illustration of a vertical cross section of a single plasma reactor 109, enclosed in a casing 204. The casing 204 may be cylindrical, or any suitable shape. For example, in FIG. 2B, a slab-shaped casing 204 is illustrated. The slap-shaped casing includes a plurality of throughholes 218 into which the other components of the reactor 109 may be fitted. The slab-shaped casing 204 is particularly useful for operating a plurality of plasma reactors 109.

The specific features of any given plasma reactor 109, are illustrated in greater detail in FIG. 2A. Various embodiments of the reactor 109 provide simple construction from pre-fabricated materials. An added benefit to such embodiments is that they can be considered "disposable."

The reactor 109 can include a body portion 217 having one or more internal walls 213, 214 that define an internal cavity 215. For a tubular geometry internal walls 213 and 214 may be the same wall. According to various embodiments, and as shown in FIG. 2, the body portion 217 may be cylindrical. Other geometric shapes are possible.

The reactor 109 can include at least one electrically-conductive inlet capillary 201 having an inlet capillary body 207 extending between a fluid-receiving tip 208 and a fluid-injecting tip 209. The fluid-receiving tip 208 is positioned outside the internal cavity 215, and the fluid-injecting tip 209 is positioned inside the internal cavity 215.

The reactor can include at least one electrically-conductive outlet capillary 205 having an outlet capillary body 210 extending between a fluid-collecting tip 211 and a fluid-ejecting tip 212. The fluid-collecting tip 211 is positioned inside the internal cavity 215, and the fluid-ejecting tip 212 is positioned outside the internal cavity 215.

The electrically-conductive inlet capillary 201 and the electrically-conductive outlet capillary 205 can be made of any electrically conductive material, for example, according to one particularly preferred embodiment the electrically-conductive inlet capillary 201 and the electrically-conductive outlet capillary 205 can be made of 316 stainless steel capillary tubing with an outer diameter (O.D.) of 1.59 mm. Other electrically-conductive materials, as described herein can also be employed. The capillaries can also be any shape, but are preferably cylindrical.

The fluid injecting tip 209 can be disposed relative to the fluid collecting tip 211 to generate a flowing liquid film region 203 on the one or more internal walls 213, 214 and a gas stream or a gas flow region 202 flowing through the flowing liquid film region 203, when a fluid is injected into the internal cavity 215 via the at least one electrically conductive inlet capillary 201. The fluid injecting tip 209 can be disposed relative to the fluid collecting tip 211 to propagate a plasma discharge along the flowing liquid film region 203 between the at least one electrically-conductive inlet capillary 201 and the at least one electrically-conductive outlet capillary 205. According to various embodiments, the fluid injecting tip 209 can be aligned with the fluid collecting tip 211.

According to particularly preferred embodiments, the internal walls 213, 214 can be defined by the inner walls of the casing 204. As discussed above, the casing 204 can take a variety of geometrical forms. The casing 204 can also be made of a variety of materials, including but not limited to glass materials, plastic materials, and crystalline materials. Some exemplary material include, glass, polytetrafluoroethylene, polyethylene terephthalate, and fused quartz. Fused quartz or fused silica is glass consisting of silica in amorphous (non-crystalline) form.

Fused silica is particularly preferred, at least in part, because it provides a wide transparency range, a low electrical conductivity, a high melting point, a high thermal conductivity, and a low thermal expansion coefficient. Generally, the higher the thermal expansion coefficient and the lower the thermal conductivity, the more sensitive the substance is to quick changes in temperature. The extremely low coefficient of thermal expansion of fused quartz, i.e., about $5.5 \times 10^{-7}$/° C. (20-320° C.), accounts, at least in part, for its remarkable ability to undergo large, rapid temperature changes without cracking.

According to certain embodiments, the casing 204 may be a substantially optically transparent material. Differing degrees of optical transparency are possible. As used herein, "optically transparent" refers to a material or layer that transmits rays of visible light in such a way that the human eye may see through the material distinctly. One definition of optically transparent is a maximum of 50% attenuation at a wavelength of 550 nm (green light) for a material or layer, e.g., a layer 1 µm thick. Another definition can be based on the Strehl Ratio, which ranges from 0 to 1, with 1 being a perfectly transparent material. Exemplary optically transparent materials can have a Strehl Ratio≥0.5, or a Strehl Ratio≥0.6, or a Strehl Ratio≥0.7, or a Strehl Ratio≥0.8, or a Strehl Ratio≥0.9, or a Strehl Ratio≥0.95, or a Strehl Ratio≥0.975, or a Strehl Ratio≥0.99.

The casing 204 may have an electrical conductivity within a range having a lower limit and/or an upper limit. The range can include or exclude the lower limit and/or the upper limit. The lower limit and/or upper limit can be selected from about $10^{-11}$, about $10^{-12}$, about $10^{-13}$, about $10^{-14}$, about $10^{-15}$, about $10^{-16}$, about $10^{-17}$, about $10^{-18}$, about $10^{-19}$, about $10^{-20}$, about $10^{-21}$, about $10^{-22}$, about $10^{-23}$, about $10^{-24}$, and about $10^{-25}$ Siemens/meter. For example, according to certain preferred embodiments, the casing 204 may have an electrical conductivity in a range of from about $10^{-11}$ to about $10^{-25}$ Siemens/meter. Other materials having similar electrical conductivities may also be employed. A casing 204 comprising glass may have an electrical conductivity in a range of from about 10-11 to about $10^{-15}$ S/m. A casing 204 comprising polytetrafluoroethylene may have an electrical conductivity in a range of from about $10^{-25}$ to about $10^{-23}$ Siemens/meter. A casing 204 comprising polyethylene terephthalate will generally have an electrical conductivity on the order of $10^{-21}$ Siemens/meter.

The casing 204 may have a melting point within a range having a lower limit and/or an upper limit. The range can include or exclude the lower limit and/or the upper limit. The lower limit and/or upper limit can be selected from about 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375, 1400, 1425, 1450, 1475, 1500, 1525, 1550, 1575, and 1600 degrees Celsius. For example, according to certain preferred embodiments, the casing 204 may have a melting point in a range of from about 300 degrees Celsius to over 1600 degrees Celsius. Other materials having similar melting points may also be employed. A casing comprising polytetrafluoroethylene, for example, may have a melting point of about 327 degrees Celsius. A casing comprising glass may have a melting point of about 1500 degrees Celsius. A casing comprising fused quartz may have a melting point of about 1600 degrees Celsius.

The casing 204 may have a thermal conductivity within a range having a lower limit and/or an upper limit. The range can include or exclude the lower limit and/or the upper limit. The lower limit and/or upper limit can be selected from about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5 W/m-K. For example, according to certain preferred embodiments, the casing 204 may have a thermal conductivity of from about 0.1 to about 5.0 W/m-K. Other materials with similar thermal conductivities may be employed. A casing comprising glass may have a thermal conductivity of from about 0.5 to about 1.0 W/m-K. A casing comprising fused quartz may have a thermal conductivity of about 1.3 W/m-K.

The casing 204 may have a thermal expansion coefficient within a range having a lower limit and/or an upper limit. The range can include or exclude the lower limit and/or the upper limit. The lower limit and/or upper limit can be selected from about $10^{-7}$, about $10^{-6}$, and about $10^{-5}$ per degree Celsius. For example, according to certain preferred embodiments, the casing 204 may have a thermal expansion coefficient of from about $10^{-7}$ to about $10^{-5}$ per degree Celsius. Other materials having similar thermal expansion coefficients may be employed. A casing comprising fused quartz may have a thermal expansion coefficient of about $5.5 \times 10^{-7}$ per degree Celsius. A casing comprising polytetrafluoroethylene may have a thermal expansion coefficient of about $1.35 \times 10^{-5}$ per degree Celsius.

As illustrated in FIG. 1A, the casing 204 may be a piece of fused quartz tubing with an I.D. of 3.0 mm (AdValue Technology), which can serve as a viewing port for emission spectroscopy and high speed imaging. According to other particularly preferred embodiments, the electrically-conductive inlet capillary 201 and the electrically-conductive outlet capillary 205 can be incased by fused quartz tubing spacers 206 with an I.D. of 1.6 mm (AdValue Technology); the tubing 206 can be positioned such that the ends of the stainless steel and quartz tube spacers are flush at the entrance and exit of the discharge region, i.e. the internal cavity 215. These inlet and outlet assemblies comprising the electrically-conductive inlet capillary 201 and the electrically-conductive outlet capillary 205 incased by fused quartz tubing spacers 206 can then inserted into either end of the tubing 204.

The fluid injecting tip 209 and the fluid collecting tip 211 (or when employed, the respective ends of the inlet and outlet assemblies) can be positioned such that a gap 216 having a length. The gap 216 can have a length within a range having a lower limit and/or an upper limit. The range can include or exclude the lower limit and/or the upper limit. The lower limit and/or upper limit can be selected from 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 20.1, 20.2, 20.3, 20.4, 20.5, 20.6, 20.7, 20.8, 20.9, 21, 21.1, 21.2, 21.3, 21.4, 21.5, 21.6, 21.7, 21.8, 21.9, 22, 22.1, 22.2, 22.3, 22.4, 22.5, 22.6, 22.7, 22.8, 22.9, 23, 23.1, 23.2, 23.3, 23.4, 23.5, 23.6, 23.7, 23.8, 23.9, 24, 24.1, 24.2, 24.3, 24.4, 24.5, 24.6, 24.7, 24.8, 24.9, and 25 mm. For example, according to certain preferred embodiments, the gap 216 can have a length of about 4 mm.

The system may also include a power source 116, supplying a voltage across the at least one electrically-conductive inlet capillary and the at least one electrically-conductive outlet capillary. The power source 116 may be adapted to provide a pulsed current, a D.C. current, and/or an A.C. current between the at least one electrically-conductive inlet capillary 201 and the at least one electrically-conductive outlet capillary 205. As illustrated in FIG. 2A, the power source 116 is electrically connected to the at least one electrically-conductive inlet capillary 201, while the at least one electrically-conductive outlet capillary 205 is grounded. The opposite arrangement is also possible, wherein the power source 116 is electrically connected to the at least one electrically-conductive outlet capillary 205, while the at least one electrically-conductive inlet capillary 201 is grounded. A wide variety of other configurations are conceivable, whereby the power source 116 can be adapted to provide a pulsed current, a D.C. current, and/or an A.C. current between the at least one electrically-conductive inlet capillary 201 and the at least one electrically-conductive outlet capillary 205.

A gap 216 separates the at least one electrically-conductive inlet capillary 201 and the at least one electrically-conductive outlet capillary 205. A ratio of the voltage supplied, i.e., the input voltage, by the power source 116 to the length of the gap 216 can be within a range having a lower limit and/or an upper limit. The range can include or exclude the lower limit and/or the upper limit. The input voltage should be sufficient to generate an electric field sufficient to produce the electrical breakdown and discharge plasma formation. The lower limit and/or upper limit can be selected from $2.5 \times 10^5$ V/m, $3 \times 10^5$, $4 \times 10^5$, $5 \times 10^5$, $6 \times 10^5$, $7 \times 10^5$, $8 \times 10^5$, $9 \times 10^5$ V/m, $1 \times 10^6$ V/m, $1.5 \times 10^6$ V/m, $2 \times 10^6$ V/m, $2.5 \times 10^6$ V/m, $3 \times 10^6$ V/m, and $3.5 \times 10^6$ V/m. For example, the gap 216 can have a length, and a ratio of the voltage to the length can be at least about $2.5 \times 10^5$ V/m or about $5 \times 10^5$ V/m.

According to certain embodiments, a combination of a gap of from about 1 to about 10 mm and an input voltage ranging from about 8 to about 20 V, can provide an average discharge voltage of about 500 V with peaks of from 1 to 3 kV. A transformer in the power supply (ignition coil) may transform the input voltage to the power supply to a much higher voltage in order to generate the electric fields mentioned above. These characteristics are exemplified in FIG. 5A. Varying the input voltage between 8 and 15 V, supplied to such embodiments, did not have a significant impact on the average discharge voltage, but did increase the current and total power. This is because of the properties of the ignition coil—increasing the input voltage increases the energy to the coil but does not change the output voltage of the ignition coil to generate the high electric fields needed to create the plasma by electrical breakdown. An average discharge voltage of about 2 kV in a gap of about 4 mm would provide 5 kV/cm as an electric field to create the discharge. Normally in air or pure gas without the liquid water stream, breakdown voltages range between 25 to 35 kV/cm and this can decrease with humidity, but not to the level obtained with a liquid stream contact.

Again, the power source 116 may be adapted to provide a pulsed current, a D.C. current, and/or an A.C. current between the at least one electrically-conductive inlet capillary 201 and the at least one electrically-conductive outlet capillary 205.

The pulsed current may have a frequency within a range having a lower limit and/or an upper limit. The range can include or exclude the lower limit and/or the upper limit. The lower limit and/or upper limit can be selected from about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 900, 1000, 1100, 1200, 1300, 1400, 1500, 1600, 1700, 1800, 1900, and 2000 Hz. For example, according to certain preferred embodiments, the pulsed current may have a frequency in a range of from about 1 Hz to about 2000 Hz. A preferred subrange is from about 100 to about 800 Hz.

The pulse may have a width of from about 0.1 ms to about 1.0 ms.

According to various embodiments the voltage supplied by the power source 116 may be brought to a sufficient level to initiate voltage breakdown and to produce a discharge channel (arc or streamer). The discharge channel characteristics such as rate of fire and on-time may be controlled via a peripheral board. The peripheral board may include a timer, which outputs a voltage pulse train based on its own input voltage level and reset characteristics.

The reaction within the reactor may be subject to the discharge channel or arc, which can be optimized/controlled by changing the peripheral board settings. The peripheral board is powered by a 12V power supply only because the timer used on this specific board calls for 4-18V power; any suitable voltage may be utilized. The peripheral board does not supply energy to the reaction it simply controls the on and off of the arc. The voltage pulse train output is sent to a switch built into an ignition coil. The ignition coil may have wires for power and for control of the power switch. The second power supply used in the present setup is merely the power for the arc itself. The peripheral board output may be tied to the switch control of the ignition coil. It should be emphasized, again, that the particular configuration described herein is merely exemplary and that a wide variety of other configurations are readily conceivable, whereby the power source 116 can be adapted to provide a pulsed current, a D.C. current, and/or an A.C. current between the at least one electrically-conductive inlet capillary 201 and the at least one electrically-conductive outlet capillary 205. Based on the particular configuration of the power supply described above, a nominally $2.5 \times 10^5$ V/m electric field is applied across two conductive electrode surfaces at (2 to 6 mm) distance apart. The voltage is of a high enough potential to overcome the separation causing an electrical discharge or arc. This arcing happens while a fluid (gas and liquid) passes between the contacts. Chemical reactions occur in and near the plasma discharge or arc. The desired product output is partly dependent on the frequency and duration of the arc and the flow, composition, and rate of the input reactants. To better control this reaction the peripheral board is utilized which allows the user to control the characteristics of the pulse train that is sent to the ignition coil's power switch. The number of reactors in a set and the number of sets used for the desired scale needed are all problem specific and can be varied as needed. The specific power supply for the larger unit will depend upon the scale required. A person having ordinary skill in the art will be readily equipped to scale the power supply, the system, and/or method disclosed herein to any desirable level. A person having ordinary skill in the art will readily appreciate that for a given input composition, flow rate, and reactor geometry, a voltage and power sufficient to produce an electrical breakdown in the gap between the electrodes which contains the water and gas mixture may be readily determined.

According to various embodiments, the body portion 217 can be cylindrical. The cylindrical body portion 217 can have a first diameter within a range having a lower limit and/or an upper limit. The range can include or exclude the lower limit and/or the upper limit. The lower limit and/or upper limit can be selected from 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, and 2 cm. For example, according to certain preferred embodiments, the cylindrical body portion 217 can have a first diameter 0.1 to 1 cm. The at least one electrically-conductive inlet capillary can have a second diameter that is less than the first diameter. The at least one electrically-conductive outlet capillary can have a third diameter that is greater than the second diameter and less than the first diameter.

FIG. 3A shows an illustration of a radial cross section along line A-A as shown in FIG. 2A of the plasma reactor 109, i.e. the discharge region, according to various embodiments. The gas flow region 202 can be bounded by a highly turbulent gas/liquid interface 301, separating the gas flow and plasma discharge region 202 from the liquid film flow region 203. As discussed under FIG. 2A, the liquid film flow region 203 flows along the casing 204, which may acts as the reactor wall.

According to various embodiments, the gas flow can be determined by the nozzle, i.e. the outlet of a capillary, diameter and the pressure. The liquid flow can be determined by the gas flow, and all other dependent properties can thereafter be determined. The maximum liquid flow can be determined by the gas flow, and all other dependent properties can thereafter be determined. The pressure of the inlet gas can be in the range of 10 to 500 pounds per square inch (psi). For an inlet gas pressure of 60 psi and a 0.01 inch inlet capillary nozzle with a 3 mm tube, the gas flow is 0.3 liters per minute and the upper liquid flow can be 4 ml/min. In addition to scaling up this process by placing many single reactors in parallel, alternative geometries could be used which utilize a single large volume chamber for the flow of water and gas in conjunction with multiple inlet and outlet nozzles into and out of the single chamber.

Figure 3B:
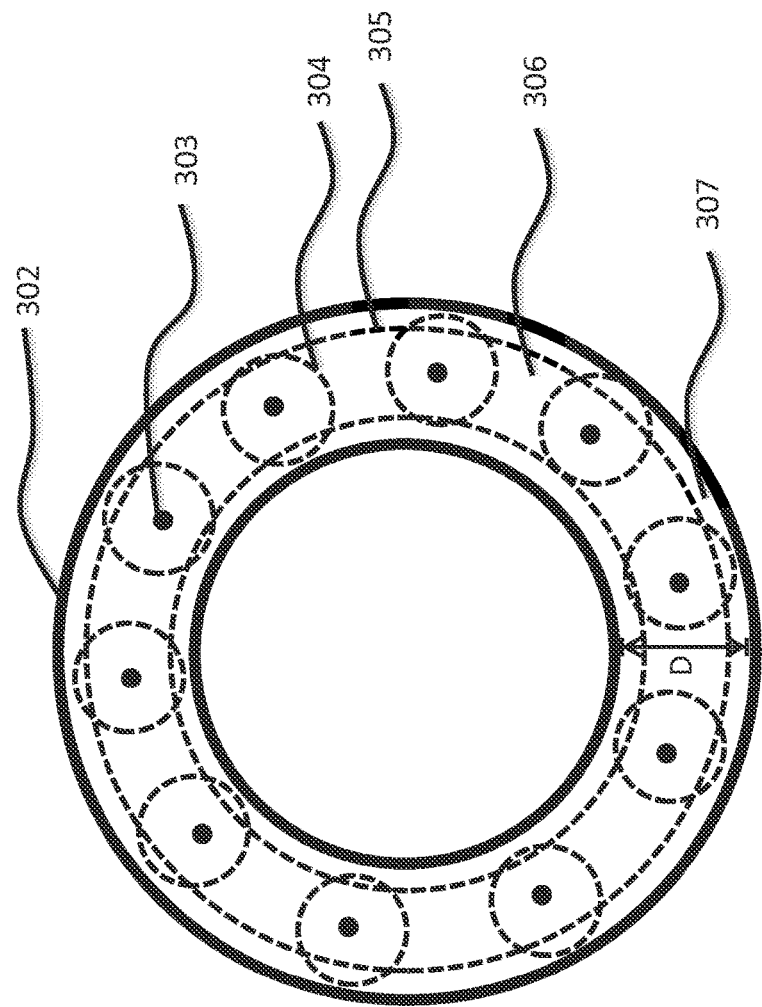

FIG. 3B shows an illustration of a radial cross section of an exemplary configuration comprising a reactor body 302 and a plurality of electrically-conductive inlet capillaries 303. The reactor body 302 is an annular ring and has a distance D between its walls. Each of the electrically-conductive inlet capillaries 303 can have a range of influence 304 within the reactor body 302. Inside its range of influence each electrically-conductive inlet capillary can be used to form a plasma discharge. One or more electrically-conductive outlet capillaries (not shown) can be aligned with or otherwise positioned relative to the plurality of electrically-conductive inlet capillaries 303 to generate a flowing liquid film region on one or more internal walls of the reactor body 302 and a gas stream or a gas flow region flowing through the flowing liquid film region, when a fluid is injected into the internal cavity via the at least one electrically conductive inlet capillary 303. The one or more electrically-conductive outlet capillaries (not shown) can additionally or alternatively be aligned with or otherwise positioned relative to the plurality of electrically-conductive inlet capillaries 303 to propagate a plasma discharge along the flowing liquid film region between one or more of the plurality of electrically-conductive inlet capillaries 303 and one or more of the one or more plurality of electrically-conductive outlet capillaries. As shown, a gas liquid interface 305 can be generated between a liquid film region 307 and a gas flow region 306 passing through the liquid film region 307.

Figure 3C:
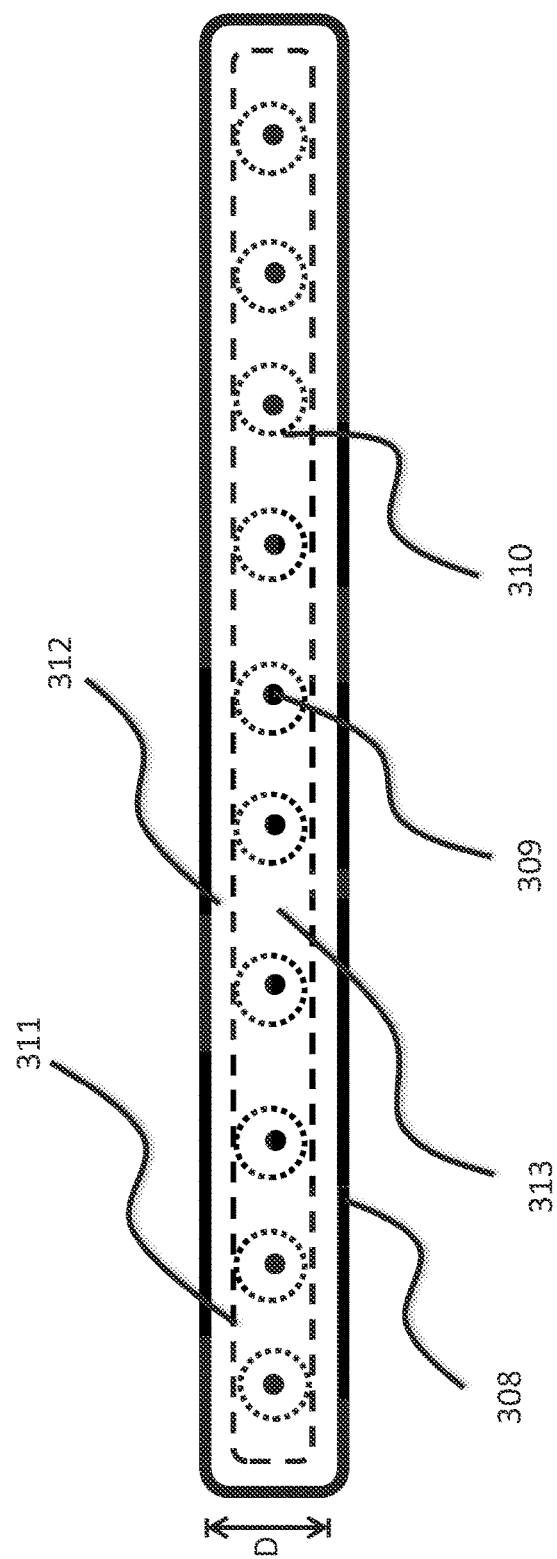

FIG. 3c shows an illustration of a radial cross section of an exemplary configuration comprising a reactor body 308 and a plurality of electrically-conductive inlet capillaries 309. The reactor body 308 is an elongated box and has a distance D between its walls. Each of the electrically-conductive inlet capillaries 309 can have a range of influence 310 within the reactor body 308. Inside its range of influence each electrically-conductive inlet capillary can be used to form a plasma discharge. One or more electrically-conductive outlet capillaries (not shown) can be aligned with or otherwise positioned relative to the plurality of electrically-conductive inlet capillaries 309 to generate a flowing liquid film region on one or more internal walls of the reactor body 308 and a gas stream or a gas flow region flowing through the flowing liquid film region, when a fluid is injected into the internal cavity via the at least one electrically conductive inlet capillary 309. The one or more electrically-conductive outlet capillaries (not shown) can additionally or alternatively be aligned with or otherwise positioned relative to the plurality of electrically-conductive inlet capillaries 309 to propagate a plasma discharge along the flowing liquid film region between one or more of the plurality of electrically-conductive inlet capillaries 309 and one or more of the one or more plurality of electrically-conductive outlet capillaries. As shown, a gas liquid interface 311 can be generated between a liquid film region 312 and a gas flow region 313 passing through the liquid film region 312.

Any configuration of the reactor body can be employed. The configurations shown in FIG. 2, FIG. 3A, FIG. 3B, and FIG. 3C are merely exemplary. A variety of geometries can be employed, but a cylindrical geometry tends to maximize contact between the discharge plasma channel and the liquid, which is desirable.

Figure 3D:
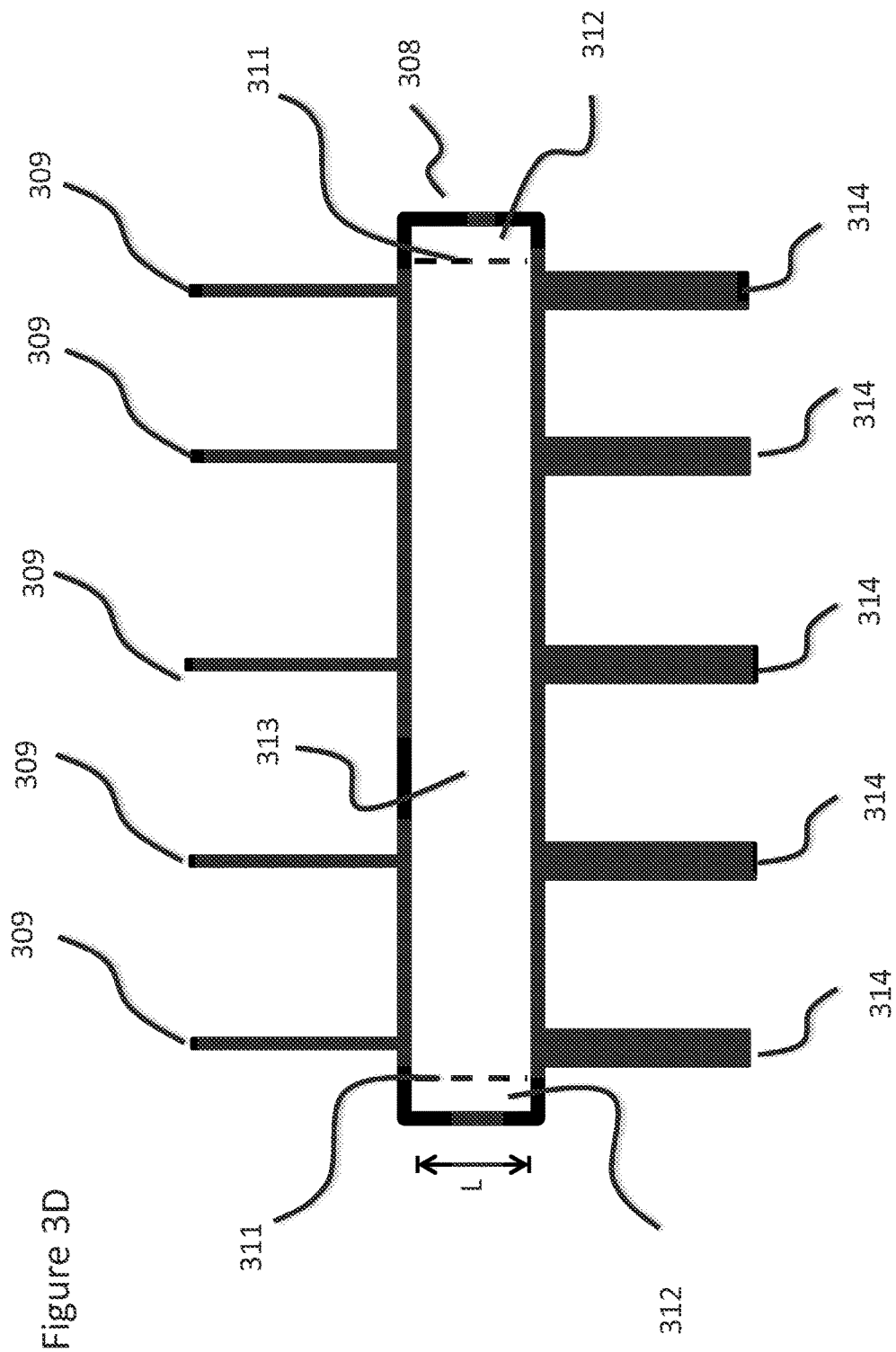

FIG. 3D shows a vertical cross-section of a reactor body 308 as depicted in either FIG. 3B or 3C. Since the cross section would be the same for both the reactor body could have been designated with reference numeral 302. Reference numerals in the specific embodiment shown in FIG. 3d correspond to those in FIG. 3c. Again, since the cross section would be the same for FIG. 3b, the reference numerals of FIG. 3b could have been used. FIG. 3d also shows a plurality of electrically-conductive outlet capillaries 314. The electrically-conductive outlet capillaries 314 are shown in alignment with the electrically-conductive inlet capillaries 309. FIG. 3c also illustrates a length L of the reactor body 308.

Figure 4B:
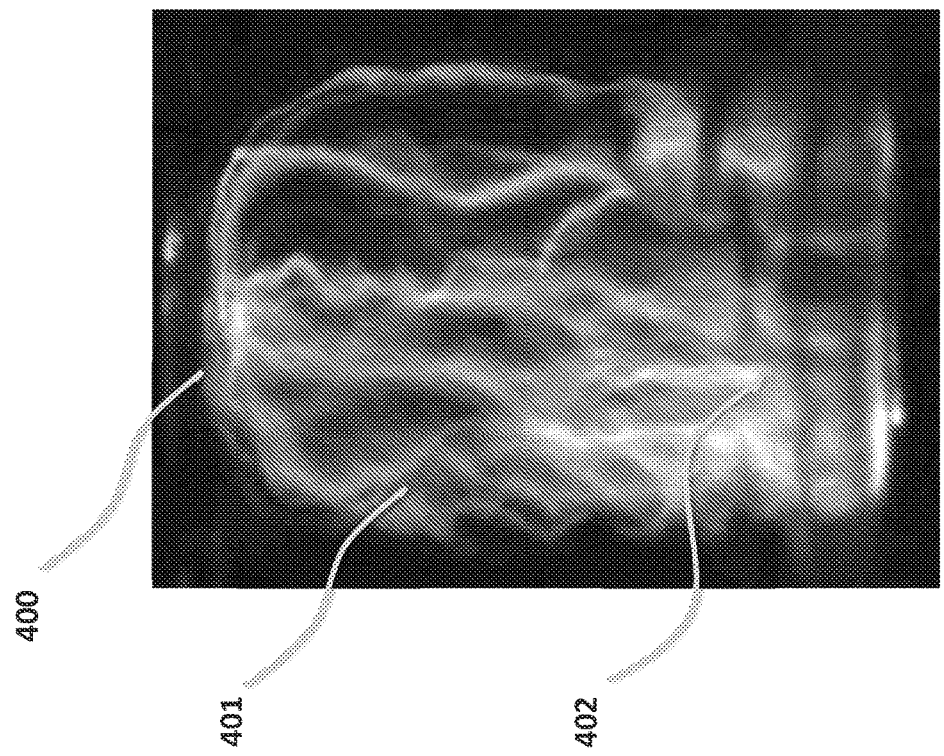
FIG. 4A-C: are photographs of the plasma discharge with a) rapid shutter speed ($1/12000$ sec) b) a long exposure time ($1/60$ sec), c) a view showing the liquid/gas interface.
Figure 4A:
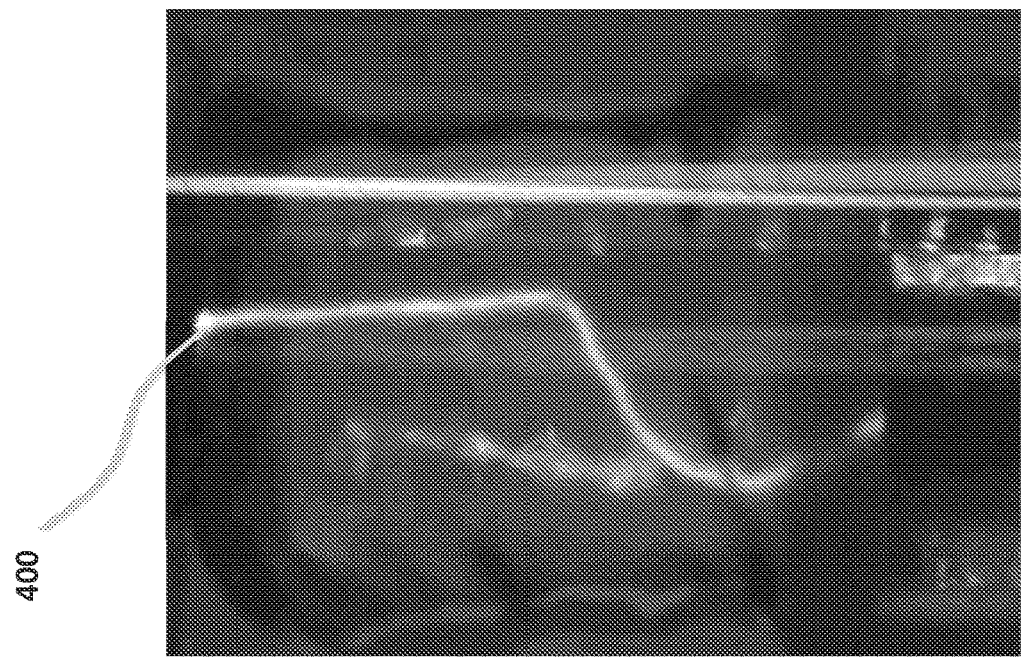
Figure 4C:
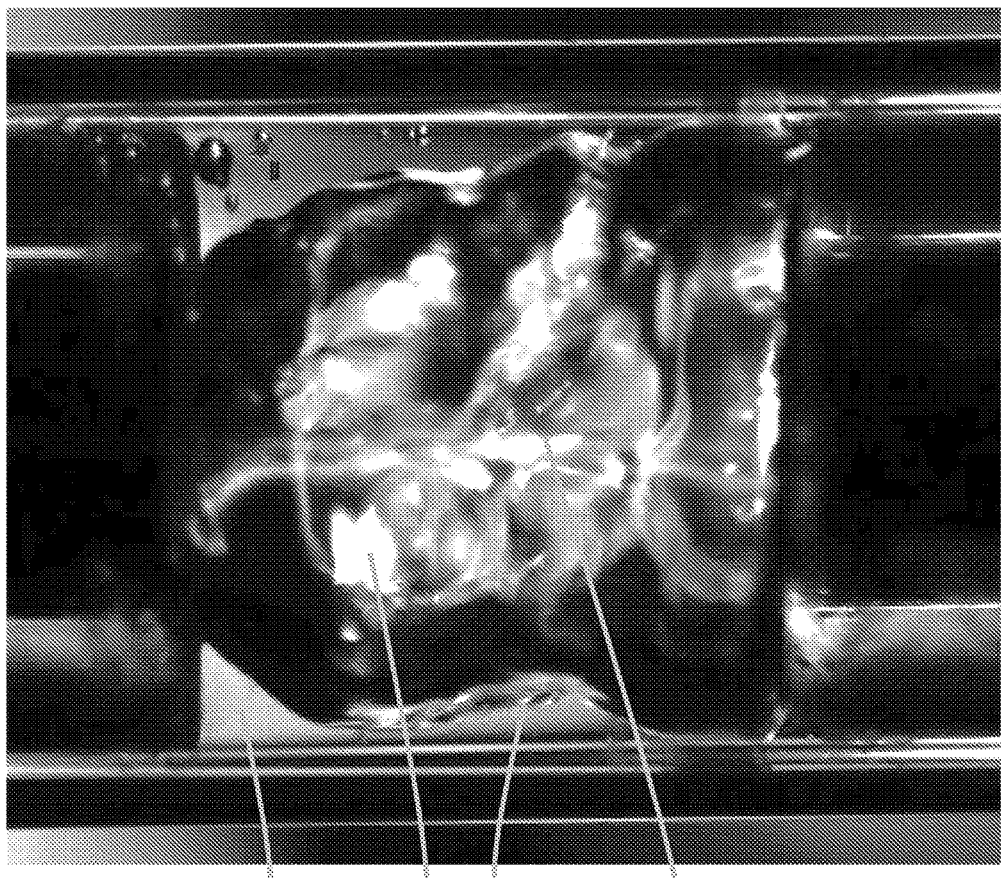

FIGS. 4a, 4b, and 4c depict high speed imaging of the plasma discharge region. FIG. 4a shows a single plasma channel 400 propagating between electrodes and along the gas liquid interface. FIG. 4b, with a long photographic exposure, shows multiple plasma channels 400, 401, and 402 propagating between electrodes. FIG. 4c shows a liquid film region 403, and a gas flow region 404, separated by a liquid/gas interface 405. A plasma discharge 406 is also shown at the liquid/gas interface 405.

EXAMPLES

Reactor and Apparatus

The examples employ a process as illustrated in FIG. 1A, which shows the general process schematic of the experimental setup. The reactor 109 was the reactor illustrated in FIG. 2A. High purity air and/or argon gas (Air Gas; Tallahassee, Fla.) at 414 kPa was utilized where the volumetric flow rate was measured by a rotameter (Cole Palmer; Vernon Hills, Ill.). The carrier gas was allowed to flow unrestricted into the reactor inlet. The gas flow rate is a function of the pressure head and the inner diameter (I.D.) of the reactor inlet nozzle.

The carrier gas then contacted a liquid stream of deionized water (pH—5.0±0.2, conductivity—5.0±1.0 µS/cm) at mixing zone 103 (1/16" Swagelok® nylon tee joint, Jax Fluid System Technologies; Jacksonville, Fla.). The deionized water was delivered to the system with a high pressure, pulse injection pump 101 (Optos Series, Eldex Laboratories Inc.; Napa, Calif.).

High pressure mixing occurred between these three components mixing zone 103, after which the mixture flowed through the inlet nozzle of the reactor 109 and into the plasma discharge region 112 where chemical reactions were induced. After exiting the discharge region 112, the liquid phase of the effluent was directly collected in a vessel.

The reactor according to this Example was constructed from pre-fabricated round tubing giving it a cylindrical geometry. FIG. 2A shows a vertical cross section diagram of the reactor. Because of its simple construction from pre-fabricated materials, an added benefit to this reactor design is that it can be considered "disposable." The inlet and outlet parts of the reactor were made of 316 stainless steel capillary tubing with an outer diameter (O.D.) of 1.59 mm (Supelco; Bellefonte, Pa.) and are incased by fused quartz tubing spacers with an inner diameter (I.D.) of 1.6 mm (AdValue Technology; Tucson, Ariz.); the tubing was positioned such that the ends of the stainless steel and quartz tube spacers were flush at the entrance and exit of the discharge region. The inlet and outlet assemblies were then inserted into either end of a casing, i.e., an additional piece of fused quartz tubing with an I.D. of 3.0 mm (AdValue Technology; Tucson, Ariz.) which served as the reactor wall and viewing port for emission spectroscopy and high speed imaging 114. The inlet and outlet assemblies were positioned such that a 4 mm gap existed between the entrance and exit of the discharge region. A horizontal cross section of the discharge region is shown in FIG. 3A.

A key aspect of this reactor system is the flow pattern generated inside the reactor volume. Because the inlet capillary tube had an internal diameter smaller than that of the discharge region, a well-mixed radial spray was generated as the high pressure mixture exited the inlet nozzle and entered the reactor volume. This spray then rapidly contacted the reactor wall creating a liquid film which flowed along the reactor wall coupled with a high velocity gas flow region in the radial center of the reactor.

High speed imaging was performed with a VW-9000 series high speed microscope system with a VH-00R 0-50× lens (Keyence; Itasca, Ill.) to confirm the existence and analyze the previously mentioned flow regions. FIG. 4A is a photograph of the reaction plasma zone region taken with a rapid shutter speed (1/12000 sec) and captures not only a single filamentous plasma channel, but also the wave-like pattern of water flow on the walls of the reactor. FIG. 4B depicts a long exposure time (1/60 sec) and captures the many filamentous plasma channels produced during this time period. Both photos (FIGS. 4A and 4B) indicate that the discharge takes place along the gas-liquid interface and not within the liquid film flow region or in the middle of the gas stream; the majority of the plasma streamers appear to travel along the highly turbulent gas liquid interface.

An additional key aspect of this reactor design was that the stainless steel capillary tubing which acted as the entrance and exit to the reactor volume also function as the anode and cathode which generate the plasma discharge. This configuration provides maximum contact of the reactants with the plasma by minimizing by-pass regions where the gas-liquid flow does not contact the plasma. In the specific setup, the high voltage lead was attached to the inlet nozzle of the reactor while the outlet capillary was grounded, as shown in FIG. 1A.

The power supply 116 (DC 1740B BK Precision; Yorba Linda, Calif.) was driven by a pulse generator (2 MHz 4010A BK Precision; Yorba Linda, Calif.) to provide pulsed 12 V direct current to an automobile ignition coil (VW-AG, ERA Germany). A high voltage diode was placed between the ignition coil and the reactor to protect the coil from unwanted upstream voltage surges back to the ignition coil from the reactor. The pulse frequency and duty cycle was held constant for all experiments at 500 Hz and 40%.

Additional tests were also performed, and similar results were obtained, using the same reactor configuration, but with a power supply 900 as illustrated in FIG. 9. The power supply 900 is only provided for exemplary purposes and is only one possible configuration. Indeed, since similar results were obtained, power supply 900 demonstrates that any suitable power supply may be employed. The power supply 900 included a 12 V DC power source 901, a pulse generator 902 operating at a frequency of from 100 Hz to 1 kHz at 10 to 50% DC; and an ignition coil system 903.

A constant DC power supply can also be used to sustain a discharge between the anode and cathode. In this situation the highly turbulent gas liquid interface is used to vary the spatial position of the generated plasma arc.

Sample current, voltage, and power waveforms when a pulsed power supply is utilized are shown in FIGS. 5A-I. FIG. 5A shows the very rapid raise in voltage and FIG. 5B shows the current pulse over about 0.5 ms with an approximate triangular shaped decay. Power is determined by the product of voltage and current as in FIG. 5C. FIGS. 5D through 5I are magnifications of the pulses showing more detail of the first pulse in FIG. 5A. FIG. 5J, FIG. 5K, and FIG. 5L show the voltage, current, and power wave forms, respectively, for the case of the air carrier gas at 0.5 l/min with deionized water (introduced conductivity 2.22 microSiemens/cm and initial pH 4.46) flowing at 0.75 ml/min. Because of the higher water conductivity (outlet conductivity 245 microSiemens/cm) formed by the nitrogen oxides the pulses are smoother, with less oscillation following the initial peak in the pulse as shown in the argon case. The pulse width is smaller with the air than argon, approximately 0.2 ms in air compared to the 0.5 ms pulse in argon with less variability between pulses in air. The maximum voltage is approximately 6.5 to 7 kV in air and it is more consistent between pulses. Other pulse shapes are possible, but the exact shape depends not only on the power supply but also the reactor and the properties (conductivity) of the gas and liquid inside the reactor. The voltage, current, and power waveforms of the discharge were measured with a Tektronix DPO 3014 oscilloscope (Tektronix Inc.; Beaverton, Oreg.). The sampling rate of the oscilloscope was $10^4$ points for the 100 ms acquisition window. The discharge voltage was measured with a high-voltage probe (P6015 Tektronix; Beaverton, Oreg.) connected to the lead electrode. The current was measured with a 100Ω shunt to the ground in the secondary of the ignition coil. The math function of the oscilloscope was used to generate the calculated power pulses. Averages of three power measurements for each trial were taken to reduce the error of the measurement and exported to a spreadsheet where the magnitude of the individual data points were averaged to provide a mean power for the time period of the acquisition window. The instantaneous power was calculated by multiplication of the individual data points in the current and voltage waveforms. The mean discharge power was determined by averaging the instantaneous power across the time period of acquisition window. It should be noted that the power reported in this study was the "power delivered to the discharge" and that the overall efficiency also depends upon the power and efficiency of the transformer.

Chemical Analysis

The concentration of hydrogen peroxide formed in the liquid fractions was measured using a colorimetric test with a UV-Vis spectrophotometer (Perkin-Elmer, Lambda 35; Waltham, Mass.) where 2 mL liquid samples were taken and mixed with 1 mL of a titanium oxysulfate-sulfuric acid complex.[86] The absorbance of the formed yellow complex was measured at a 410 nm wavelength and converted to hydrogen peroxide concentration by a calibration curve generated with stock solutions of hydrogen peroxide where concentration was confirmed by titration with 0.1 N potassium permanganate.

The concentration of nitrate formed was measured by ion chromatography. A calibration curve was generated with standard solutions of known nitrate concentration.

FIG. 6 depicts the concentration, production rate, and energy yield for hydrogen peroxide generation as well as discharge power for the various water flow rates when only argon is used as the carrier gas. The concentration portion of this figure clearly shows an increase in hydrogen peroxide concentration as the water flow rate was decreased. When the production rate of hydrogen peroxide was calculated from multiplication of these concentrations by their corresponding water flow rate it can be seen to be relatively stable around 0.07 μmol/s across the range of water flow rates tested. From this figure the discharge power can also be seen to be fairly stable around 0.25 W across the range of flow rates. Because there is relatively no change in discharge power or production rate as a function of water flow rate, when the production rate is divided by the power to arrive at an energy yield, the values similarly show little variation with flow rate with an average at 33 g/kWh.

Figure 7A:
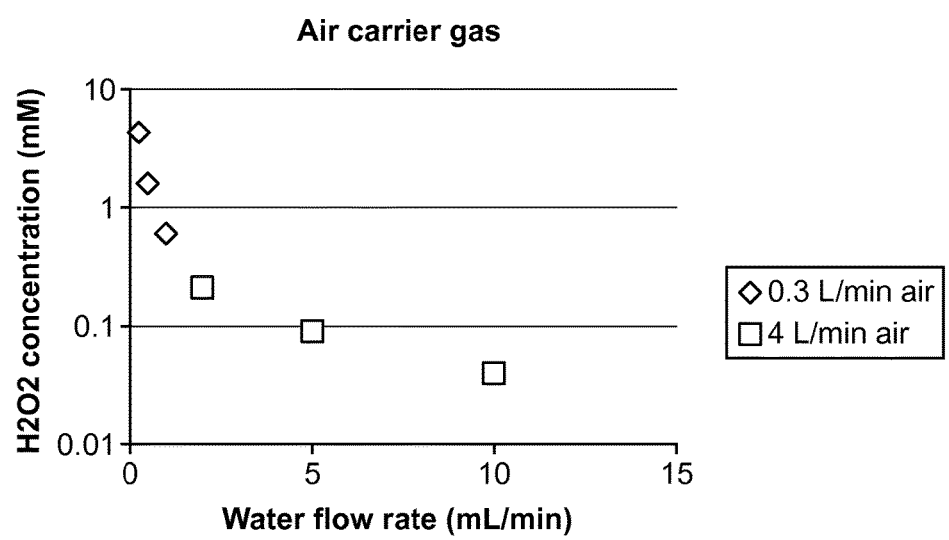
FIG. 7A-B: are charts showing the concentration and production rate of hydrogen peroxide for various water and gas flow rates when air is utilized as the carrier gas.
Figure 7B:
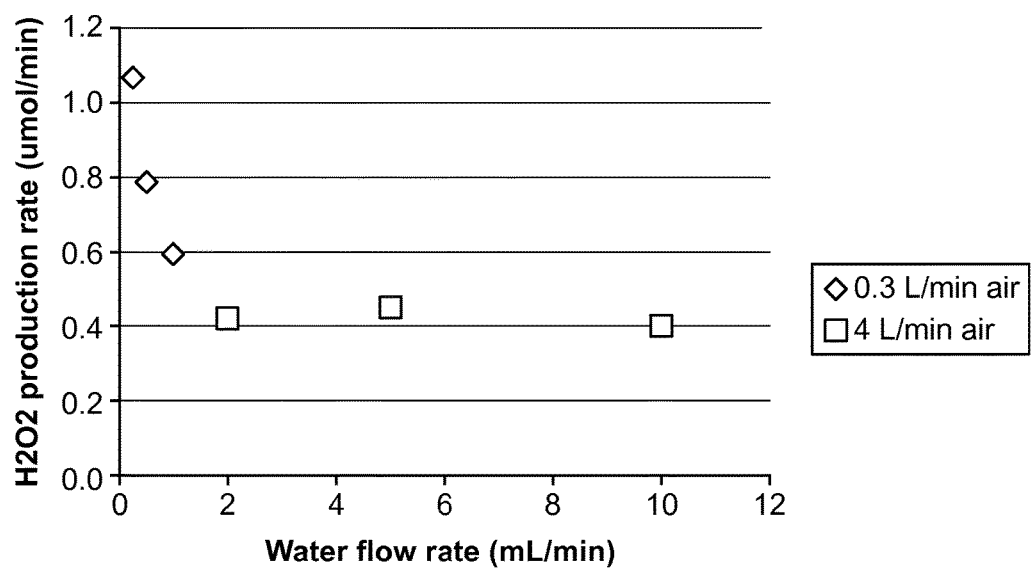

FIG. 7 shows the concentration and production rate of hydrogen peroxide generated when only air is used as the carrier gas. Clearly the amount of hydrogen peroxide generated significantly decreases when air utilized due to the presence of additional reactive chemical species which can react with the formed hydroxyl radicals. It should be noted however that the production rate of hydrogen peroxide significantly increases when the flow rates of air and water are reduced.

Figure 8A:
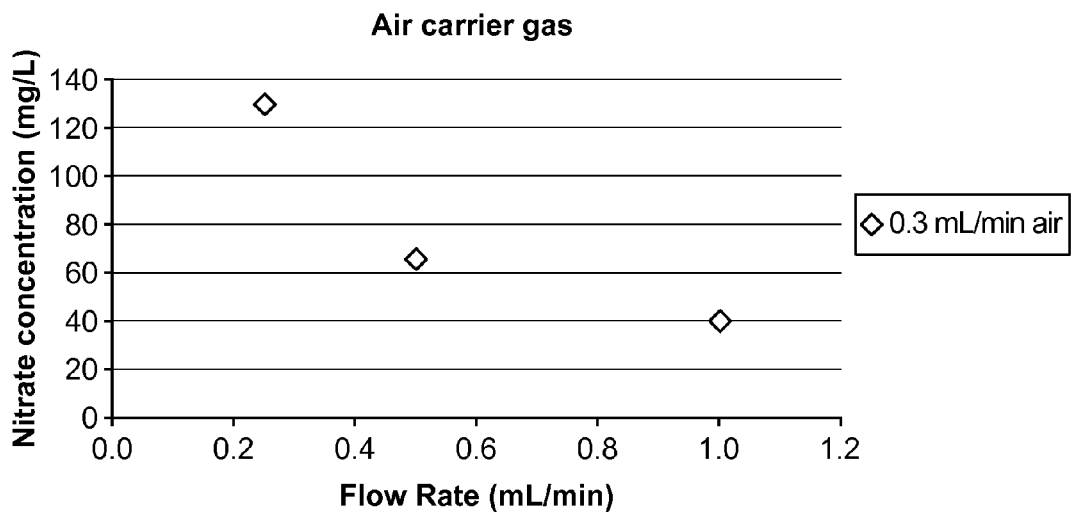
FIG. 8A-B: are charts showing the concentration and production rate of nitrate for various water and gas flow rates when air is utilized as the carrier gas.
Figure 8B:
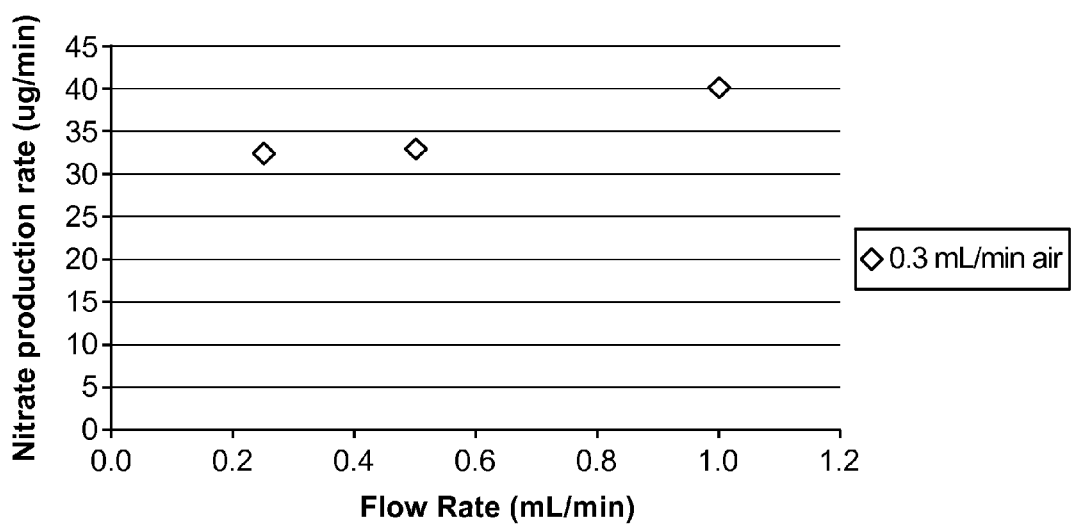
Figure 9A:
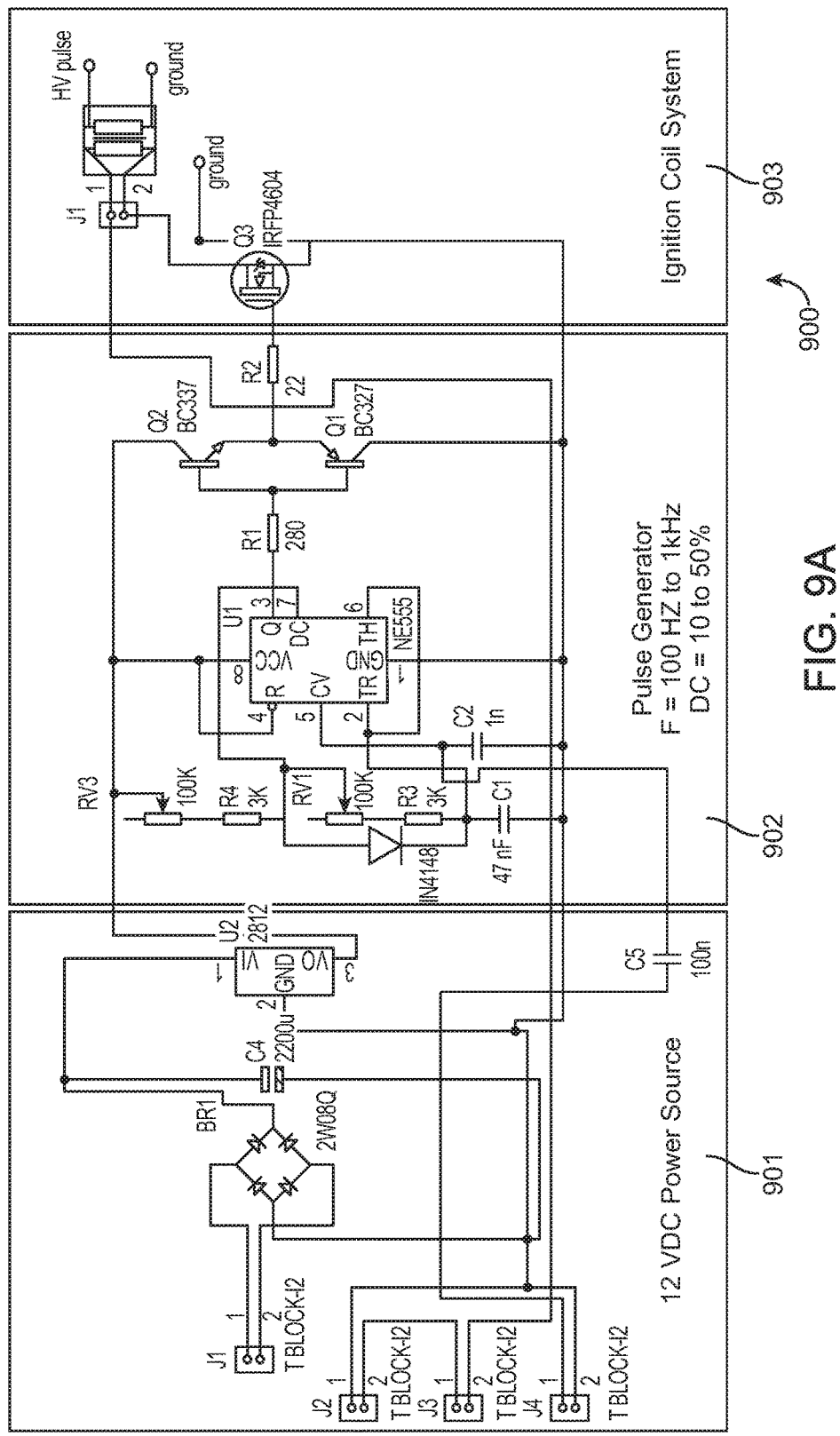
FIG. 9A: is an exemplary circuit diagram of a power supply, including a power source, a pulse generator, and an ignition coil system, according to various embodiments.
Figure 9B:
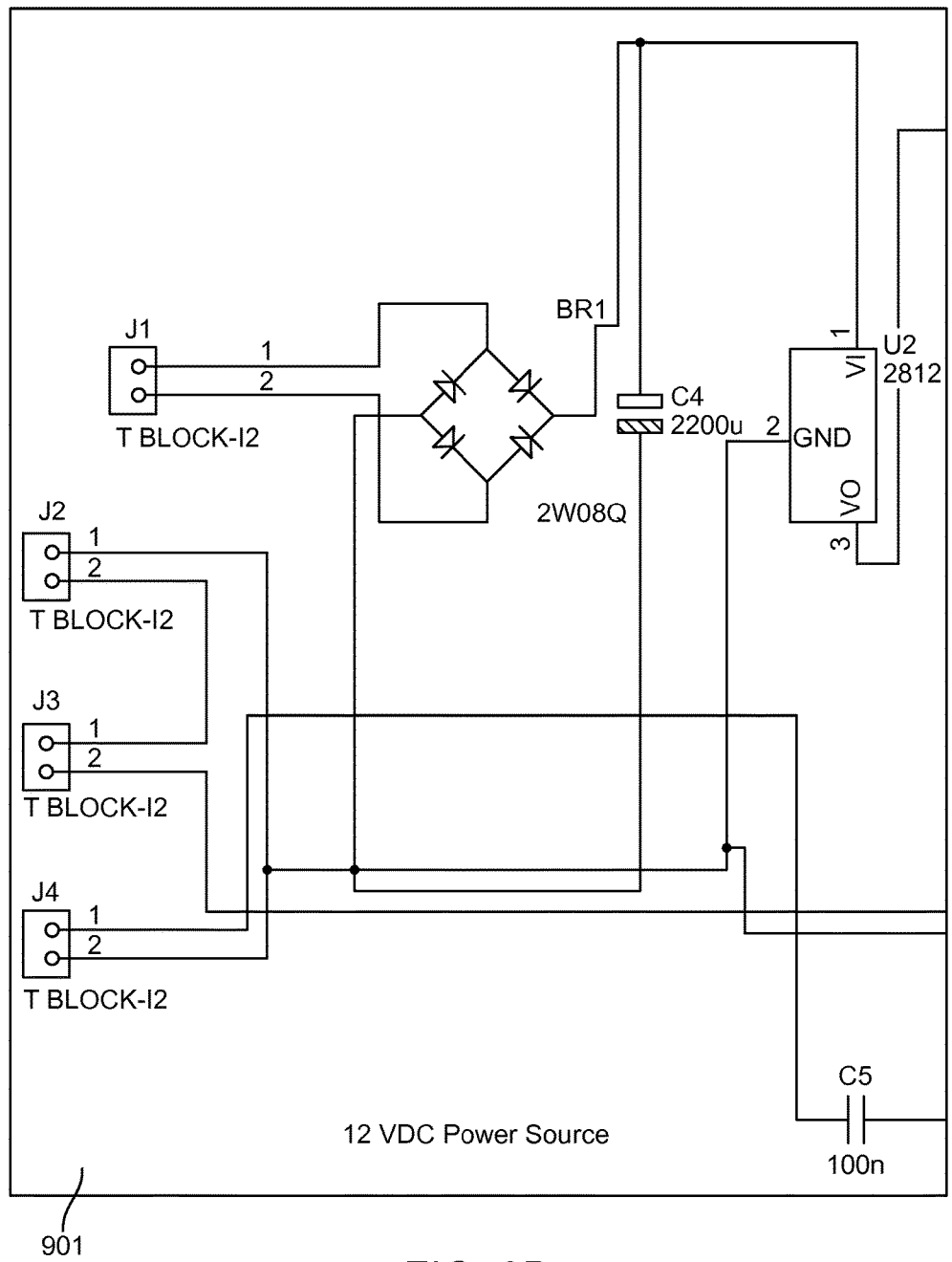
FIG. 9B: is an enlarged view of the power source shown in FIG. 9A.
Figure 9C:
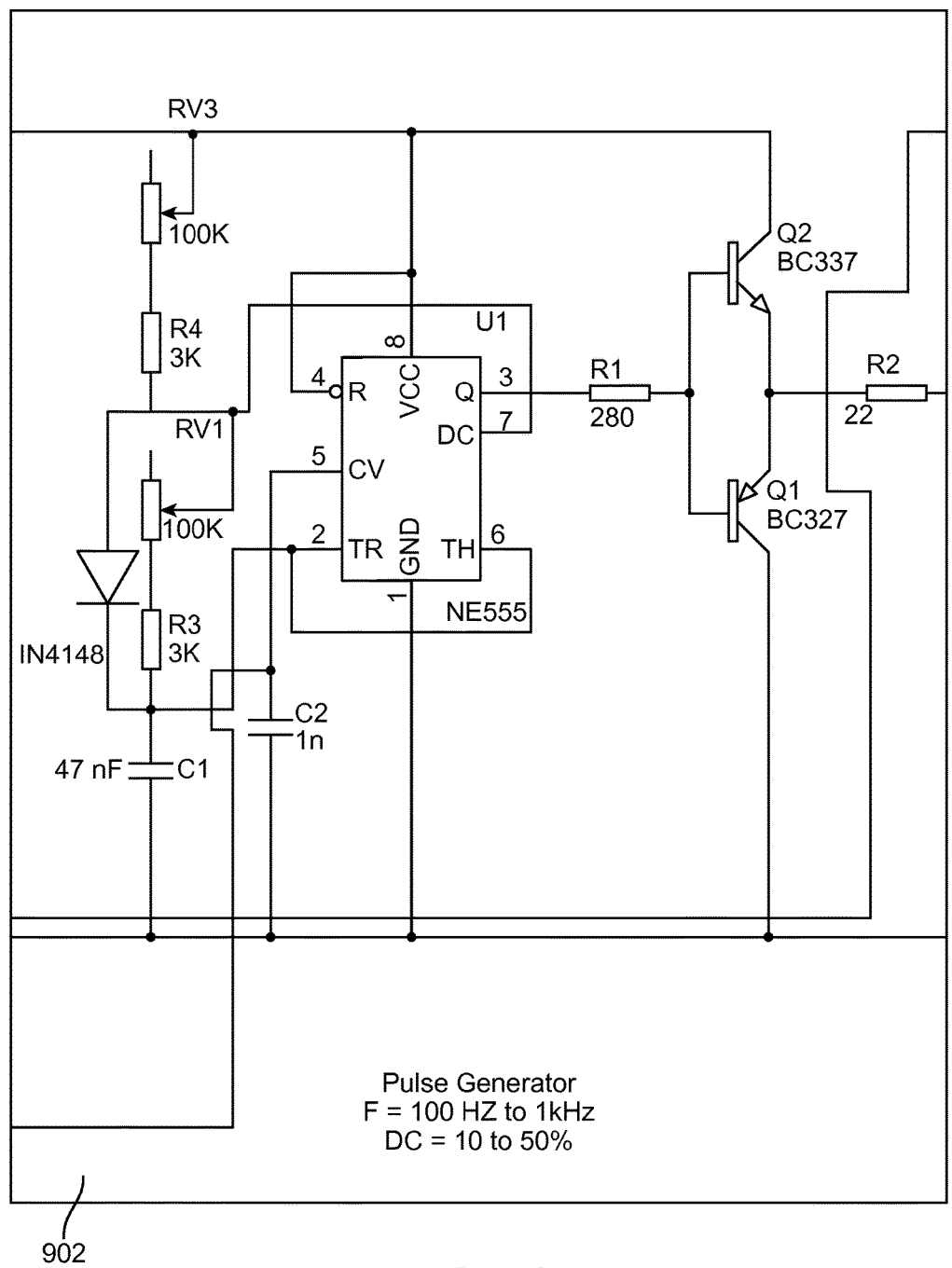
FIG. 9C: is an enlarged view of the pulse generator shown in FIG. 9A.
Figure 9D:
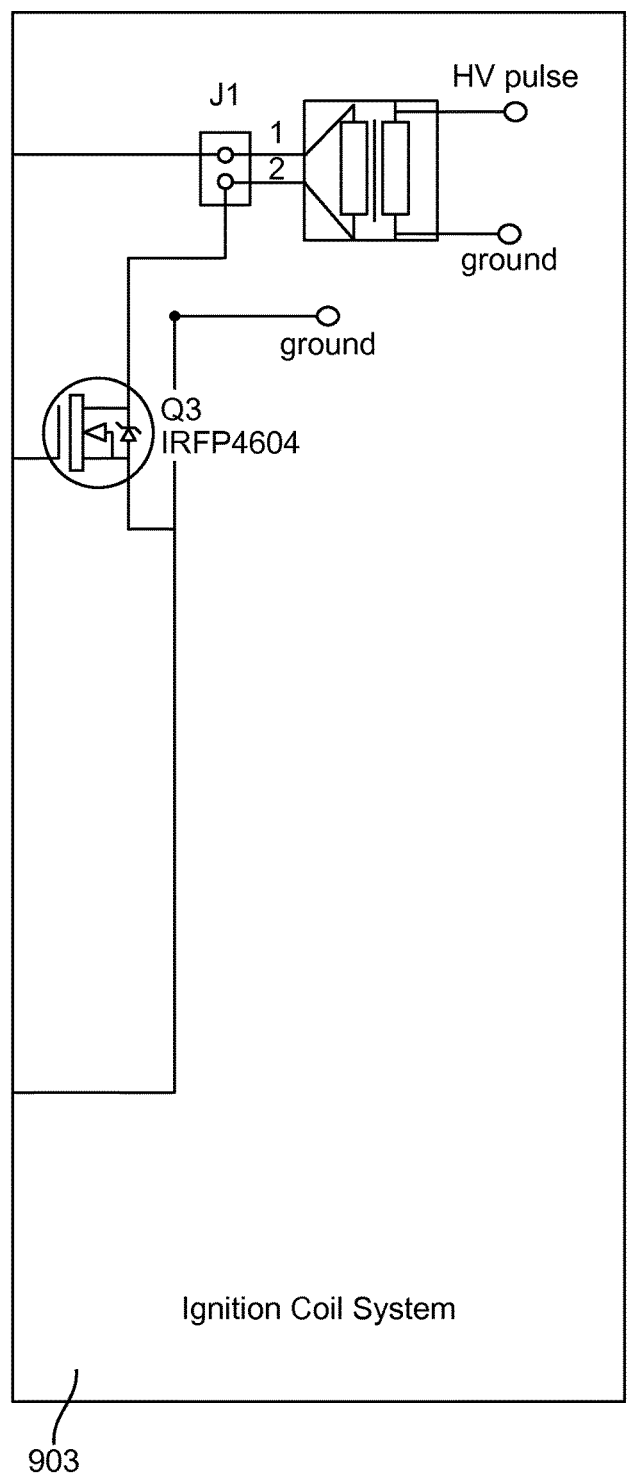
FIG. 9D: is an enlarged view of the ignition coil system shown in FIG. 9A.

FIG. 8 depicts the formation of nitrate for various water flow rates when air is used as the carrier gas. This figure shows that the concentration of nitrate increases when the water flow rate is decreased. However, the production rate of nitrate production rate does not significantly decrease when the water flow is decreased indicating that dilution effects are the likely cause of the decrease in concentration at the higher water flow rates.

Although the present invention has been described in considerable detail with reference to certain preferred versions thereof, other versions are possible. Therefore, the spirit and scope of the appended claims should not be limited to the description of the preferred versions contained herein. All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

What is claimed is:

1. A reactor system comprising:
   a liquid source;
   a gas source;
   a casing having a plurality of internal cavities; and
   a plurality of reactor assemblies arranged in parallel, wherein each of the plurality of reactor assemblies comprises:
   at least one electrically-conductive inlet capillary having an inlet capillary body extending between a fluid-receiving tip and a fluid-injecting tip, wherein the fluid-receiving tip is positioned outside one of the plurality of internal cavities, and wherein the fluid-injecting tip is positioned inside one of the plurality of internal cavities, and wherein the fluid-receiving tip of the inlet capillary is fluidly connected to the liquid source and the gas source to receive a liquid and a gas;
   at least one electrically-conductive outlet capillary having an outlet capillary body extending between a fluid-collecting tip and a fluid-ejecting tip, wherein the fluid-collecting tip is positioned inside one of the plurality of internal cavities, and wherein the fluid-ejecting tip is positioned outside one of the plurality of internal cavities, wherein the inlet capillary, the outlet capillary, and the internal cavity are configured to generate a flowing liquid film region on an internal wall of one of the plurality of internal cavities and a gas stream flowing through the flowing liquid film region, when the liquid and the gas are injected into the internal cavity via the at least one electrically conductive inlet capillary, and wherein the inlet capillary, the outlet capillary, and the internal cavity are configured to propagate a plasma discharge along the flowing liquid film region between the at least one electrically-conductive inlet capillary and the at least one electrically-conductive outlet capillary.

2. The reactor system according to claim 1, further comprising a power source, supplying a voltage across the at least one electrically-conductive inlet capillary and the at least one electrically-conductive outlet capillary.

3. The reactor according to claim 2, wherein the power source is adapted to provide a pulsed current between the at least one electrically-conductive inlet capillary and the at least one electrically-conductive outlet capillary.

4. The reactor system according to claim 2, wherein the power source is adapted to provide a D.C. current between the at least one electrically-conductive inlet capillary and the at least one electrically-conductive outlet capillary.

5. The reactor system according to claim 2, wherein the power source is adapted to provide an A.C. current between the at least one electrically-conductive inlet capillary and the at least one electrically-conductive outlet capillary.

6. The reactor system according to claim 2, wherein a gap separates the fluid-injecting tip and the fluid-collecting tip, wherein the gap has a length, and wherein a ratio of the voltage to the length is at least about $2.5 \times 10^5$ V/m.

7. The reactor system according to claim 1, wherein the fluid injecting tip is aligned with the fluid collecting tip.

8. The reactor system according to claim 1, wherein the casing is optically transparent and wherein the reactor system further comprises an imaging apparatus disposed adjacent to the casing and adapted to capture imaging information of the flowing liquid film region.

9. The reactor system according to claim 1, wherein the casing comprises fused quartz.

* * * * *